(12) United States Patent
Chatley et al.

(10) Patent No.: US 8,522,252 B2
(45) Date of Patent: *Aug. 27, 2013

(54) LOAD BASED FILE ALLOCATION AMONG A PLURALITY OF STORAGE DEVICES

(75) Inventors: Scott P. Chatley, San Diego, CA (US); Thanh T. Phan, San Diego, CA (US); Troy C. Gatchell, San Diego, CA (US)

(73) Assignee: Nirvanix, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/595,959

(22) Filed: Aug. 27, 2012

(65) Prior Publication Data

US 2012/0323844 A1  Dec. 20, 2012

Related U.S. Application Data

(63) Continuation of application No. 12/200,836, filed on Aug. 28, 2008, now Pat. No. 8,271,992.

(60) Provisional application No. 60/968,848, filed on Aug. 29, 2007.

(51) Int. Cl.
*G06F 17/30* (2006.01)

(52) U.S. Cl.
USPC ........................................................ 718/105

(58) Field of Classification Search
None
See application file for complete search history.

(56) References Cited

U.S. PATENT DOCUMENTS

| | | |
|---|---|---|
| 6,671,259 B1 | 12/2003 | He et al. |
| 7,020,698 B2 | 3/2006 | Andrews et al. |
| 7,546,354 B1 | 6/2009 | Fan et al. |
| 2003/0065763 A1 | 4/2003 | Swildens et al. |

OTHER PUBLICATIONS

PCT/US2008/074778 International Search Report and Written Opinion mailed Mar. 24, 2009, 8 pages.
English-Language Machine Translation of KR-10-2006-0104310 (Inventor Kim) as performed by KIPO, publ. date Oct. 19, 2006, 10 pages.
Foldoc: "least recently used" article. Feb. 15, 1995, 1 page.

*Primary Examiner* — Robert Fennema
(74) *Attorney, Agent, or Firm* — Duane Morris LLP

(57) ABSTRACT

A method for balancing loads among a plurality of data storage devices, includes: receiving a request from a user device to download a data file; identifying a first set of storage devices containing the requested data file, wherein the first set comprises one or more storage devices; identifying a first storage device from the set that is currently least busy among the storage devices in the first set, and directing the first storage device to serve the request; determining if the first storage device is too busy; and if the first storage device is too busy copying the requested data file to a second storage device which did not previously store the data file, thereby adding the second storage device to the first set of storage devices containing the requested data file.

12 Claims, 21 Drawing Sheets

Virtual Folder Table

| Folder ID | Folder Name | PFID |
|---|---|---|
| 1 | Scott | 0 |
| 2 | Music | 1 |
| 3 | Video | 1 |
| 4 | Movies | 3 |
| 5 | Rich | 0 |
| 6 | Movies | 5 |

*FIG. 4A*

Virtual File Table

| File ID | File Name | PFID | LFID |
|---|---|---|---|
| 12345 | Pirates | 4 | 101 |
| 6789 | Caribbean | 6 | 101 |

*FIG. 4B*

Virtual Metadata Table

| File ID | Metadata Type |
|---|---|
| 6789 | xyz |

Logical File Table

| LFID | Media Key (Hash) | File Size |
|------|------------------|-----------|
| 101  | AC47BF           | 400MB     |
| 102  | X543CT1          | 2MB       |
| -1   | ?                | ?         |

Logical Node Table

| LFID | Node ID | Online |
|------|---------|--------|
| 101  | 1       | 1      |
| 101  | 2       | 0      |
| 101  | 3       | 1      |

| LFID | Metadata Type |
|------|---------------|
| 101  | ABCD          |

| Geocode ID | Priority ID | Node ID |
|---|---|---|
| 1 | 1 | A |
| 1 | 1 | B |
| 2 | 1 | A |
| 2 | 2 | B |
| 3 | 1 | B |
| 3 | 2 | A |
| 4 | 2 | A |
| 4 | 2 | B |
| 5 | 2 | B |
| 5 | 3 | A |
| 6 | 2 | A |
| 6 | 3 | B |

1072, 1074, 1076

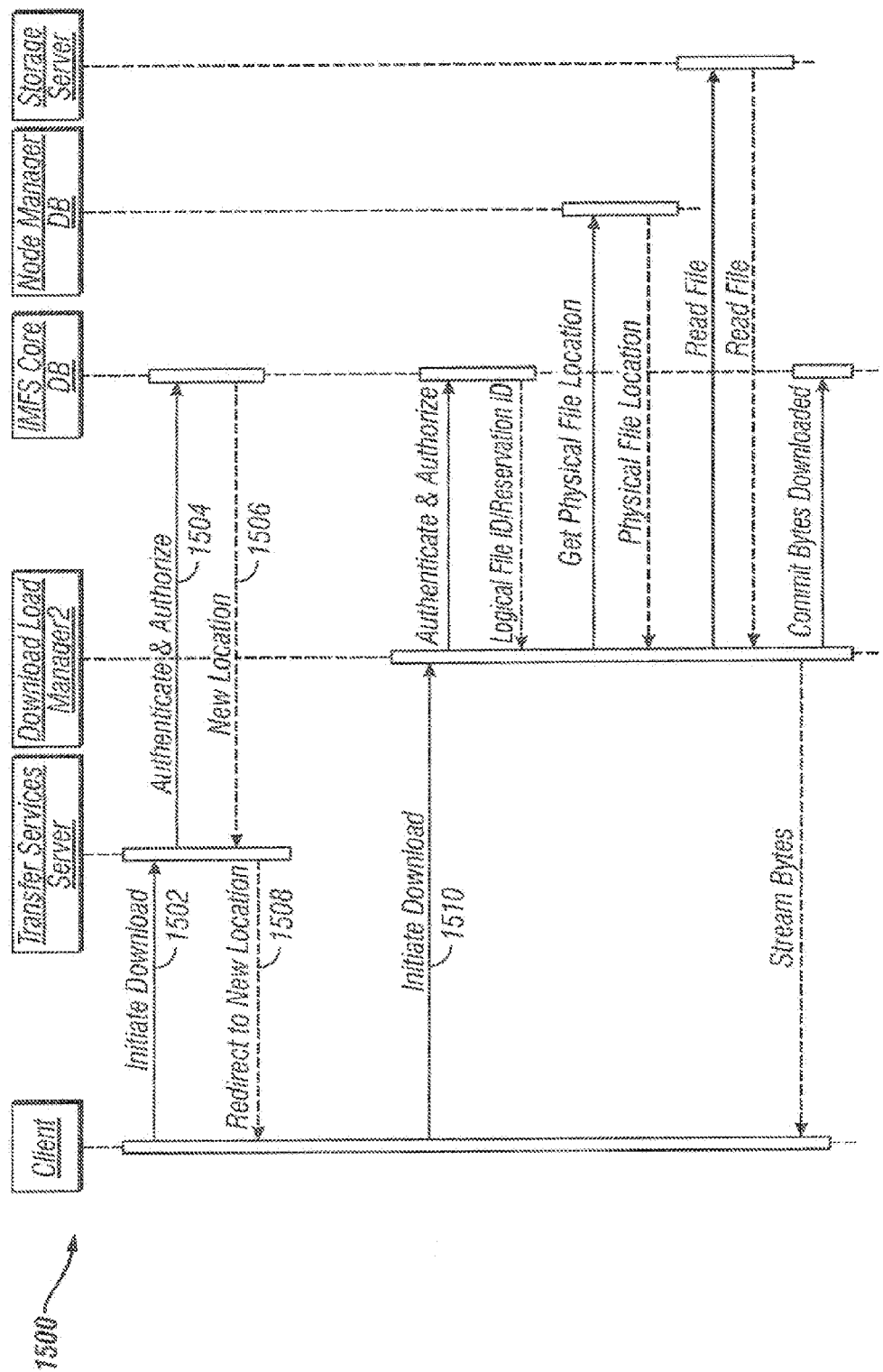

LOAD BASED FILE ALLOCATION AMONG A PLURALITY OF STORAGE DEVICES

CROSS-REFERENCE TO RELATED APPLICATIONS

This application is a Continuation of application Ser. No. 12/200,836 filed Aug. 28, 2008 now U.S. Pat. No. 8,271,992, which claims priority to U.S. Provisional Patent Application No. 60/968,848 filed Aug. 29, 2007, the contents of which are incorporated by reference herein in their entireties.

FIELD OF THE INVENTION

The present invention relates generally to data storage, and more particularly to a method and system for storing, accessing and manipulating data in a data communications network.

BACKGROUND OF THE INVENTION

In computing, a file system can store and organize data files in order to make the data files easier to find and access. File systems may use a data storage device such as a hard disk or CD-ROM to maintain the physical location of computer files. A file system may provide access to data on a file server by acting as a client for a network protocol. In other words, file system can be a set of abstract data types that are implemented for the storage, hierarchical organization, manipulation, navigation, access, and retrieval of data.

A network file system is a file system that acts as a client for a remote file access protocol, providing access to files on a server. A network file system can be any computer file system that supports access of files over a computer network. A network file system may be distributed over clients, servers, and storage devices dispersed among the machines distributed in an intranet or over the internet. Service activity occurs across the network, and instead of a single centralized data repository, the system may have multiple and independent storage devices. In some network file systems, servers run on dedicated machines, while in others a machine can be both a server and a client. A network file system can be implemented as part of a distributed operating system, or by a software layer that manages the communication between conventional operating systems and file systems. A network file system may appear to its users to be a conventional, centralized file system. The multiplicity and dispersion of its servers and storage devices can be made invisible, and the client interface used by programs should not distinguish between local and remote files. It is up to the network file system to locate the files and to arrange for the transport of data.

A storage delivery network (SDN) may include a network file system that is used for scalable networking applications. SDNs can be composed of one or more storage nodes, each node containing one or more servers for storing data files and at least one transfer server for serving files and/or media over a network. In one embodiment, the transfer server and a storage server may be implemented by a single server.

SUMMARY OF THE INVENTION

Embodiments of the invention are directed to methods and systems for storing, accessing, manipulating and controlling folders and/or files over the internet by utilizing three control layers: a virtual layer, a logical layer and a physical layer. As known in the art, a "folder" may store one or more "files" and a "file" typically, but not necessarily, stores a predetermined amount of information, data or media content (e.g., a single document, movie, or music/song file).

In one embodiment of the present invention, a file system is accessed, controlled and manipulated over the internet via requests to web services (e.g., SOAP or REST). These web services interact with one or more database servers, referred to herein as file system database servers or "core servers," which provide for virtualization of the file system and mapping of a virtual layer to a logical layer, which in turn is mapped to a physical layer.

In one embodiment, user information such as file names, path names, metadata, etc. is stored in a virtual layer or virtual file system (VFS), which allows users to share access to the same common physical file but assign it individual names, locations and metadata (extended properties) within the system. During normal access (e.g., move, copy, delete, rename, etc), the VFS increases speed of file manipulation by eliminating the necessity of "touching" the physical file itself. Rather, the user's directory structure is controlled through the file system database server and the data is stored within a series of tables. A web services layer of the system presents the accessing user a tree-structured file system and allows the user to manipulate the system in a familiar fashion.

In a further embodiment, access to a user's file system is secured so that only authorized users with the correct permissions, in accordance with each user's account information (e.g., Application Name/User Name) can access the directory structure and the files within each folder. In extended circumstances, users may have the ability to create "public shares" and grant or restrict access to shared files or folders by entities external to the SDN, as the user sees fit.

In a further embodiment, names or references to files stored within the VFS are mapped to references stored in a logical file system (LFS). This is the layer which allows the system to de-duplicate the common elements of user inputted files as opposed to simple de-duplication of the file itself. Files have certain intrinsic properties that do not change from user to user, such as embedded metadata, file size, file type. Once a file is uploaded to the system, this information typically does not change, though it may be overridden by the user. Information stored within the LFS is intrinsic to the file, and when a file has different information stored within it, even though the files may appear to be identical to an end user, the virtue of the different embedded data makes them different for purposes of de-duplication. However, as explained in further detail below, if a user chooses to over-ride metadata (e.g., run time of a video) or other intrinsic information contained within a file, the newly created metadata or information is stored in a separate metadata table in the VFS and does not effect the metadata stored in the LFS. Thus, the presence of both the VFS and LFS allows de-duplication of the common elements of a file (e.g., the actual content itself) even if a user desires to over-ride other portions of the file such as metadata. From the perspective of the user, the file has been customized to his or her preference. However, for storage purposes the file itself can still be stored and referenced by a plurality of users.

Beneath the LFS, lies the physical file system (PFS) where the files actually reside. The files are stored within one or more servers within one or more nodes. In one embodiment, the logical file system need only contain information determining which node(s) each of the files is stored, whereas each node contains the catalog of where each file exists on which server(s) within that node. In other words, each node autonomously controls the placement of files within itself and the LFS simply knows that the file exists somewhere within that node. As used herein, a "node" refers to a storage element containing one or more storage devices for storing files therein and providing access to files (e.g., uploading and downloading of files). In one embodiment, a node contains one or more storage servers, a node manager server for controlling and keeping track of where each file resides within the node, and one or more transfer servers (e.g., web servers) for sending or receiving files to end users.

In one embodiment, when a store, put or upload request (collectively referred to as an "upload" request) is received by the system, the VFS determines which user is adding the file and determines, for example, via geocode, node storage availability, and other criteria, which node the user should upload to and redirects the user to the proper node for upload. The user's connection to the core server is then severed and the connection is established with the designated node, which begins accepting the packets of the file. When the file upload is complete, a transfer server at the node to which the file has been uploaded, makes a request back to the VFS initiating an entry into the user's VFS, creating a folder path or virtual file for the user and assigning the new entry a temporary logical file ID (LFID) so that the user can access the newly uploaded file immediately. The transfer server then notifies the node's internal processing system by adding an entry into a processing queue.

The processing system then processes the file by applying a hashing algorithm to it, e.g., the MD5 file hashing algorithm. Once this hash is determined, a "media key" is created by logically combining the hash with the file's size in bytes. The processing system then communicates with the LFS which then determines whether or not an identical file already exists within the system. The LFS checks its database tables to determine if there is an identical media key. The LFS then determines whether the file exists "near enough" to the user requesting upload of the file via geocode comparisons. If the file does exist at a "near enough" node, the LFS notifies the VFS and the temporary LFID referenced by the VFS is replaced with the permanent LFID associated with the identical file stored in the "near enough" node. If an identical file is online and is "near enough" the LFS informs the node to mark the recently uploaded file for deletion and temporarily stores the file at a designated storage location. All uploaded files marked for deletion are cleaned up (deleted) by a daemon which crawls the system as a backend process that is transparent to the user.

If the LFS determines that the file does not previously exist in any network node, or that the file does not exist "near enough," or that the file is offline, it then extracts metadata from the file and creates logical file tags for storage in a metadata table within the LFS. The LFS then assigns a new permanent LFID to the new file and requests the designated node to place a copy of the file within a selected storage server and update the node manager database with the new LFID and location of the new physical file. The LFS also notifies the VFS of the new LFID assigned to the new file.

In a further embodiment, the invention determines whether a node or other network resource is "near enough" by determining a physical location associated with a user computer by translating its IP address into a geocode and, thereafter, comparing this geocode with a geocode associated with one or more nodes or other network resources. The method and system of the invention then assigns one or more nodes or network resources (e.g., servers) to service the user's request (e.g., an upload or download request) based at least in part on the location of the network resource relative to the location of the user's computer as determined by respective geocodes associated with the user's computer and the network resource.

As used herein a "geocode" refers to any code or value which is indicative of a geographic location of an object, device or entity associated with the geocode. One type of geocode that is known in the art is used, for example, by the U.S. postal service to assign codes to geographic regions or areas. In general, the geocode is a code that represents a geospatial coordinate measurement of a geographic location and time. A geocode representation can be derived, for example, from the following geospatial attributes: latitude, longitude, altitude, date, local time, global time and other criteria, such as, how the area is coded (e.g., number, letter, mixture of both, or other), which part of the earth is covered (e.g., whole earth, land, water, a continent, a country, etc.), what kind of area or location is being coded (e.g., country, county, airport, etc.), and/or whether an area or point is being coded. Generally, a geocode is a number representation that takes into account some or all of the above criteria.

Every computer or device that communicates over the Internet has a unique Internet Protocol (IP) address assigned to it. Computers and devices residing within a pre-determined geographic region or area are typically assigned a specified range of IP addresses. For example, all computers within Japan may have IP addresses in the range of 43.0.0.0-43.255.255.255 (Source: TANA, Japan Inet, Japan (NET-JAPAN-A).

In one embodiment, when a user or customer makes an upload (a.k.a., "put" or "store") or download (a.k.a., "get" or "retrieve") request, via a web services interface, for example, the request is received by a file system server (a.k.a., "core system server") which translates the IP address associated with the incoming request into a geocode. In one embodiment, the system looks up a table that correlates IP addresses with geocodes, or IP address ranges with geocode ranges. After the IP address has been translated into a geocode, the system compares the geocode to the geocodes that have been assigned to network resources (e.g., a storage node) within the network and determines, algorithmically, which resources are "nearest" the requestor. If only one resource is "near enough," the user is redirected to that resource. If multiple resources are "near enough," the system may determine which of the resources is currently experiencing the lightest volume of requests (e.g., via updatable polling) and redirect the requestor to that resource. Or, in an alternative implementation, the requestor may be directed to the absolute nearest resource, regardless of current volume. In one embodiment, the core system determines if a network resource is "near enough" by subtracting the geocode identified for the incoming request from the geocode associated with the target resource and determining if the absolute value of the difference exceeds a predetermined threshold. In another embodiment, whether the requester's geocode indicates the requester is near enough a resource can simply be determined by accessing a look up table (e.g., a node priority list) which assigns nodes to geocode ranges.

In one embodiment, if the user request is an upload request, when determining which network storage nodes are "closest," an amount of available storage at each storage node is taken into consideration as a factor. After the closest storage node has been selected by the core system, the user request is redirected to that node and the user may immediately begin to upload his or her file(s) to an upload server at the designated node. When an incoming file is received, the upload server temporarily stores the file in an upload cache memory while a processing system within the node processes the received file. This allows the user to access the newly uploaded file immediately via a download server at the node, if desired. Thus, there is no delay due to file processing.

In one embodiment, initial download requests (e.g., a retrieve or "get" requests) associated with a user IP address are received via a web services interface by the core system. Via geocode comparison, for example, the core system will identify the closest storage node containing the requested file and redirect the user request to that node. It should be understood that even though an online node that stores the requested file is deemed to be "closest," this does not necessarily mean it is "near enough" to the user. The designated node can then start transmitting the requested file to the user with minimum latency. As the transmission is taking place, a processing system (e.g., one or more servers) within the node determines whether the node is "near enough" based on a geocode associated with the user computer making the download request.

In one embodiment, a difference in geocode values associated with the user's computer and the storage node is indicative of a distance between the node and the requesting computer or device. If the distance exceeds a predetermined threshold, the node notifies the core system of the distance value. The core system will then determine if there are other online nodes that are "near enough" to the user and whether any of those nodes contain a copy of the requested file (in the event that a previously offline file recently came online). If there are no "near enough" online nodes that contain the file, the core system will direct the previously designated node to transfer the file to the closest of the "near enough" nodes. If there is a "near enough" online node that contains a copy of the file, the user will be redirected immediately prior to beginning his download. In an alternative implementation, all download requests begin at the core and thereafter directed to the proper node. In an alternative embodiment, whether a storage node is "near enough" the user computer may be determined by looking up a node priority table to see whether a geocode or geocode range associated with the user computer has been assigned for that node.

In one embodiment, after a near enough node has been identified in response to an initial download request, as described above, subsequent requests by the same computer system for the same file, will not go to the core system via a web services interface. Instead, the customer application interface keeps a record of the previous request and the previously identified "near enough" node, and redirects any subsequent requests for the same file by the same IP address directly to that "near enough" node. In one embodiment, a permanent redirection only takes place if a "near enough" node is found. If a requested file exists in the system, but not in a near enough node, the redirect is temporary.

In a further embodiment, additional information that can be included within a geocode, or become part of the "near enough" or distance calculation may include, for example, quality of service (QoS) as determined by a service level agreement (SLA) associated with a particular user, number of accesses to the requested file during a pre-specified period, number of accesses by the particular user, bandwidth speeds and availability, relative connectivity (i.e., how busy a node is) and master internet trunk information.

In another aspect of the invention, a method for balancing loads among a plurality of data storage devices, includes: receiving a request from a user device to download a data file; identifying a first set of storage devices containing the requested data file, wherein the first set comprises one or more storage devices; identifying a first storage device from the set that is currently least busy among the storage devices in the first set, and directing the first storage device to serve the request; determining if the first storage device is too busy; and if the first storage device is too busy copying the requested data file to a second storage device which did not previously store the data file, thereby adding the second storage device to the first set of storage devices containing the requested data file.

In a further aspect, a system for balancing loads among a plurality of storage servers within a storage node, includes: a node manager server for receiving a request from a user device to download a data file; a plurality of storage servers contained within a first storage node for storing one or more copies of the data file; a transfer server coupled to the plurality of storage servers for downloading the data file requested by users; wherein the node manager server includes: a first module for receiving the request from the user device to download the data file; a second module for identifying a first set of storage servers among the plurality of storage servers in the node containing the requested data file, wherein the first set comprises one or more storage servers; a third module for identifying a first storage server from the first set that is currently least busy among the storage servers in the first set, and directing the first storage server to serve the request; and a fourth module for determining if the first storage device is too busy, wherein if the first storage device is too busy, copying the requested data file to a second storage server which did not previously store the data file, thereby adding the second storage server to the first set of storage servers containing the requested data file.

In another embodiment, the invention provides a computer readable medium storing computer executable instructions that when executed perform a process for balancing loads among a plurality of storage servers within a storage node, the instructions including: a first code module for receiving a request from a user device to download a data file; a second code module for identifying a first set of storage servers among a plurality of storage servers in a first node containing the requested data file, wherein the first set comprises one or more storage servers; a third code module for identifying a first storage server from the first set that is currently least busy among the storage servers in the first set, and directing the first storage server to serve the request; and a fourth code module for determining if the first storage device is too busy, wherein if the first storage device is too busy, copying the requested data file to a second storage server which did not previously store the data file, thereby adding the second storage server to the first set of storage servers containing the requested data file.

BRIEF DESCRIPTION OF THE DRAWINGS

The present disclosure, in accordance with one or more embodiments, is described in detail with reference to the following figures. The drawings are provided for purposes of illustration only and merely depict typical or exemplary embodiments of the disclosure. These drawings are provided to facilitate the reader's understanding of the disclosure and shall not be considered limiting of the breadth, scope, or applicability of the disclosure. It should be noted that for clarity and ease of illustration these drawings are not necessarily made to scale.

FIGS. 4A-4C illustrate exemplary virtual file system (VFS) tables that store user information corresponding to the directory structures and path names of FIG. 3 in accordance with one embodiment of the invention.

FIGS. 5A-5C illustrate exemplary logical file system (LFS) tables in accordance with one embodiment of the invention.

FIG. 15 illustrates an exemplary file relocation and download sequence that may be implemented using an IMFS core database in accordance with one embodiment.

DETAILED DESCRIPTION OF THE EXEMPLARY EMBODIMENTS

Various embodiments of the present invention are directed toward systems and methods for storage delivery network (SDN) systems that enable users to store, retrieve, and manipulate files from a remote location using a rich set of web service application programming interfaces (APIs). Embodiments of the invention are described herein in the context of exemplary applications. As would be apparent to one of ordinary skill in the art after reading this description, these applications are merely exemplary and the invention is not limited to operating in accordance with these examples. It is to be understood that other embodiments may be utilized and structural changes may be made without departing from the scope of the present invention.

In accordance with one embodiment, an SDN system may store, access, manipulate, and control folders and/or files over the Internet by utilizing three control layers: a virtual layer, a logical layer, and a physical layer.

Figure 1:
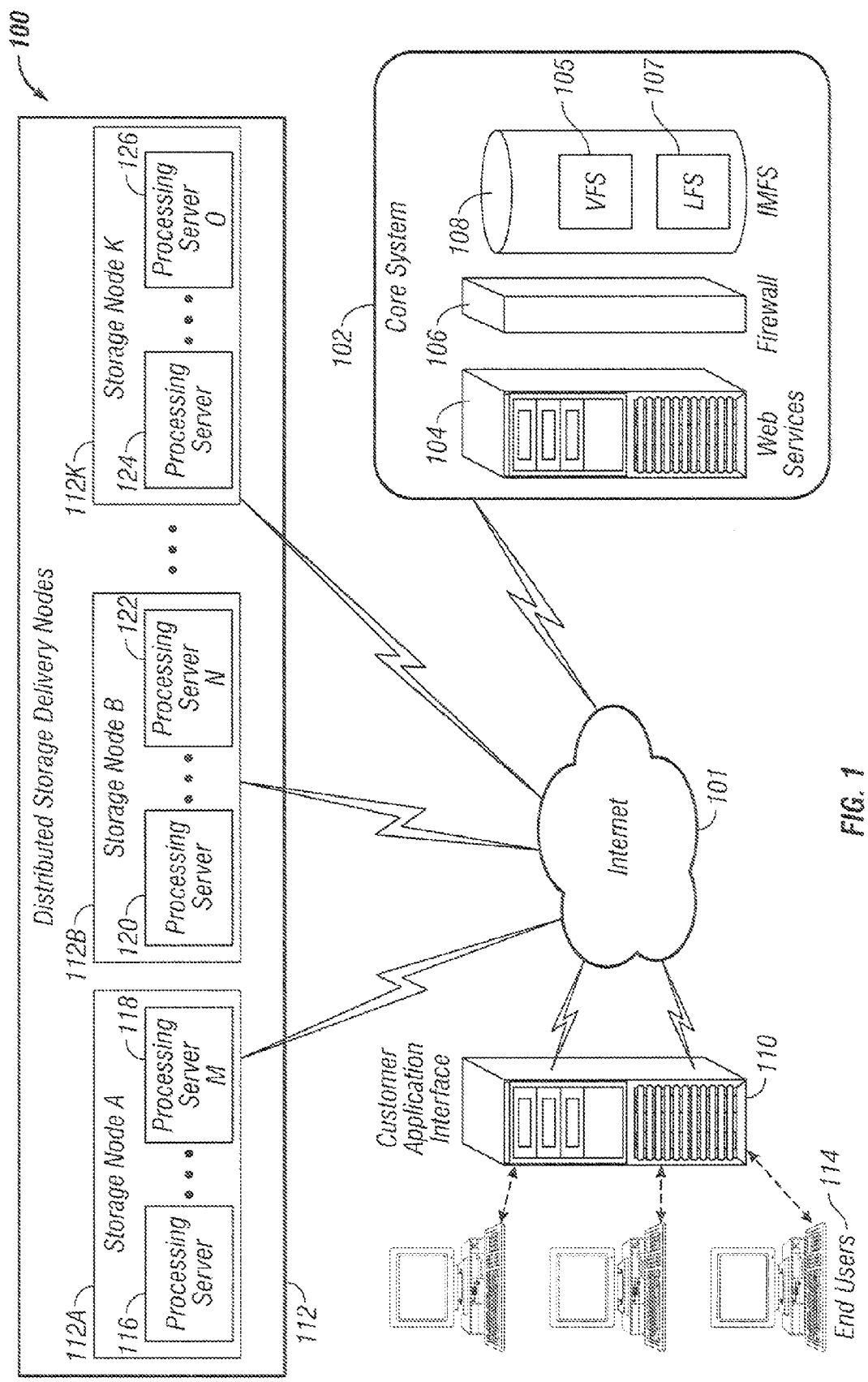
FIG. 1 illustrates an exemplary storage delivery network (SDN) system in accordance with one embodiment of the invention.

FIG. 1 illustrates an exemplary SDN system 100 in accordance with one embodiment of the invention. The SDN system 100 may comprise a core system 102, which may control one or more distributed storage delivery nodes 112A, 112BB-112K. The SDN system 100 may also comprise a customer application interface 110, which may serve a plurality of end users 114. The core system 102, the distributed storage delivery nodes 112A, 112B-112K, and the customer application interface 110 can communicate via a communication network such as the Internet 101.

The core system 102 may comprise a web services server 104, a firewall server 106, and an Internet media file system (IMFS) 108. It is understood that the core system 102 may comprise any number of servers (e.g., the web services server 104, firewall server 106) for performing its tasks and operations described herein. In addition, the various functionalities and operations described herein may be consolidated into a fewer number of servers or processors, or distributed among a larger number of servers or processors, as desired in accordance with network requirements.

The web services server 104 may accept requests from end users 114 (e.g., via customer application interface 110) related to accessing, storing and manipulating files stored on the SDN system 100. The web services server 104 may also redirect end users 114 to appropriate storage delivery nodes 112 during uploading and downloading of media files, for example.

The firewall server 106 provides a software application, which inspects network traffic passing through the web services server 104, and permits or denies passage based on a set of rules. A firewall's basic task is to regulate some of the flow of traffic between computer networks of different trust levels. Typical examples are the Internet which is a zone with no trust and an internal network which is a zone of higher trust. A firewall's function within a network is to prevent unauthorized or unwanted network intrusion to the private network.

In accordance with one embodiment, the IMFS 108 includes a computer database and computer programs that provide file system services to the web services server 104. In one embodiment, the IMFS 108 includes a virtual file system (VFS) 105, and a logical file system (LFS) 107. The IMFS 108 may organize the storage of data using a database structure, such as a relational database structure. Examples of other database structures that may be used are hierarchical database and object oriented database structures. Database management systems may be included in the IMFS 108 to organize and maintain the database. The IMFS 108 may also comprise a computer or computers dedicated to running the IMFS 108.

In one embodiment, the core system 102 communicates with a customer application interface 110 via the Internet 101 in accordance with a web services protocol (e.g., Simple Object Access Protocol (SOAP) or Representational State Transfer (REST)). The customer application interface 110 provides requested files (e.g., music or video files) and services (e.g., video streaming) to a plurality of end users 114 who have purchased or subscribed to the customer application interface. In various embodiments, the customer application interface 110 can be a hosted website on a server, or an application running on a personal computer or other computing device (e.g., a mobile phone or personal digital assistant (PDA)).

With further reference to FIG. 1, physical end user files are stored in physical file storage (PFS) distributed across storage delivery nodes 112A, 112B-112K. Each distributed storage delivery node 112A, 112B-112K may include a plurality of processing servers 1-M, 1-N and 1-O respectively (where A, B and K, and M, N and O can be any positive integer value). In one embodiment, each distributed storage delivery node 112A, 112B-112K has a node manager database server, a transfer server for handling uploading and downloading of files, one or more processing servers for processing the files, and one or more storage servers for storing files after they have been processed. An exemplary storage delivery node 112 is explained in more detail below with reference to FIG. 7.

Figure 2:
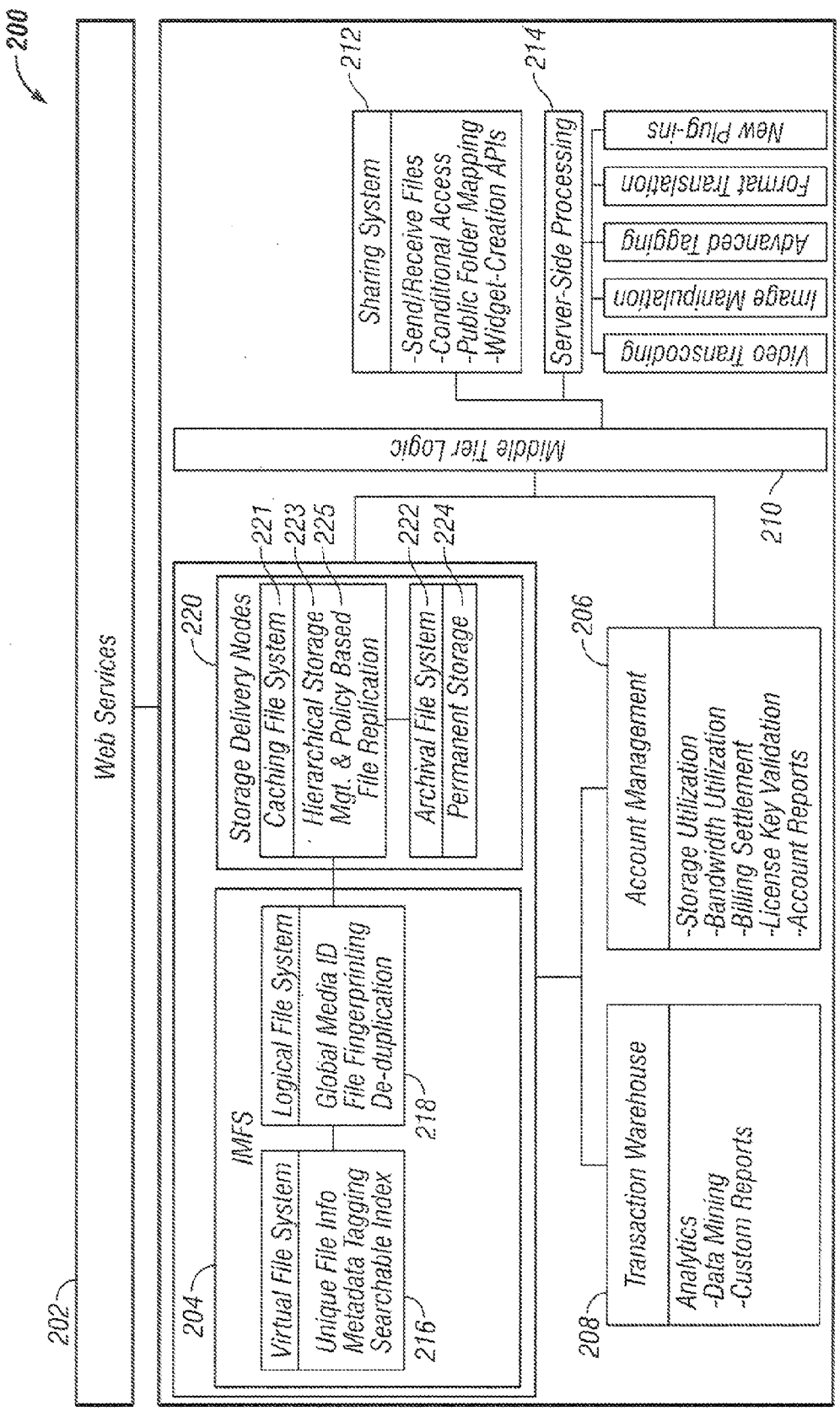
FIG. 2 illustrates a block diagram of an SDN in accordance with one embodiment of the invention.

FIG. 2 illustrates an exemplary block diagram of an SDN system 200 in accordance with one embodiment of the invention. Various elements of SDN system 200 may be identical or similar to elements of SDN system 100 of FIG. 1. SDN system 200 includes a web services subsystem 202, an IMFS 204 (similar to IMFS 108 in FIG. 1), distributed storage delivery nodes 220 (similar to storage delivery nodes 112A, 112BB-112K of FIG. 1), an account management subsystem 206, and a transaction warehouse/analytics subsystem 208. SDN system 200 may also comprise middle tier logic 210 coupled to the IMFS 204, storage delivery nodes 220, and the account management subsystem 206. SDN system 200 further includes a sharing engine subsystem 212 and server side processing applications 214. Each of these systems and applications are described in further detail below.

The web services subsystem 202 can provide an application program interface (API) to end users 114 (FIG. 1) via the Internet 101. In exemplary embodiments, the web services subsystem 202 operates industry standard REST and/or SOAP protocols allowing end users 114 to upload, copy, move and delete files and folders. Furthermore, end users 114 can retrieve a listing of their files stored in SDN system 200 and associated user defined tags and metadata. In one embodiment, the web services subsystem 202 presents the end user 114 with a tree-structured file system allowing the end users 114 to store and access files in a familiar fashion. In one embodiment, the file system is presented to the end user as a virtual hard drive on the end user's computing device. Communications between the end users 114 and core system 102 servers (FIG. 1) can use the Hypertext Transfer Protocol over Secure Socket Layer (HTTPS) protocol.

With further reference to FIG. 2, the IMFS 204 can include a Virtual File System (VFS) 216 and a Logical File System (LFS) 218 for managing files stored on the SDN system 200.

The VFS 216 can function as an abstraction layer on top of one or more conventional file systems to provide a uniform interface that is used to access data or files from one or more storage locations via a communications network. For example, VFS 216 can be an abstraction of a physical file storage system implementation, providing a consistent interface to multiple file and/or storage systems, both local and remote. In other words, the VFS 216 can allow end users 114 to access different types of file or file systems in a uniform way. The VFS 216 can, for example, be used to access local and remote network storage devices transparently without the client application noticing the difference. Additionally, in one embodiment, the VFS 216 can be used to bridge the differences in various types of file systems, so that client applications can access files on local or remote file systems without having to know what type of file systems directly control access to those files. Thus, the consistent interface provided by VFS 216 can allow the end users 114 to uniformly interface with a number of diverse file system types.

The VFS 216 stores end user information and controls end user directory structures (e.g., a tree structure) presented to end users 114 accessing files stored in SDN system 200. Directory structures can be presented to the end users 114 via the web services subsystem 202. As will be explained in further detail below, the VFS 216 includes a database that stores tables populated with information related to user files stored on the SDN system 200. For example, these tables can be populated by user folder names (e.g., "Scott's music"), user assigned file names (i.e., virtual file name), user overridden metadata, directory and/or path information, as well as virtual file identification (VFID) values associated with stored files. The VFID can be used to correlate each virtual file name with logical file and/or physical file information.

The LFS 218 provides an application with a consistent view of what can be, for example, multiple physical file systems and multiple file system implementations. In one embodiment, file system types, whether local, remote, or strictly logical, and regardless of implementation, are indistinguishable for applications using LFS 218. A consistent view of file system implementations is made possible by the VFS 216 abstraction. The VFS 216 abstraction specifies a set of file system operations that an implementation includes in order to carry out LFS 218 requests. Physical file systems can differ in how they implement these predefined operations, but they present a uniform interface to the LFS 218.

The LFS 218 stores information about files stored on SDN system 200, such as a media key (e.g., hash key), metadata, file size, file type, and the like. The LFS 218 also stores a logical file identification (LFID) value that is used to correlate or link a corresponding VFID with one or more physical files located in the distributed storage delivery nodes 112A, 112B-112K (FIG. 1). Thus, the LFS 218 acts as an intermediate layer that correlates the virtual layer with the physical layer. It is appreciated that many VFIDs may correspond to a single LFID, which in turn may correspond to one-to-many physical files distributed in various geographically distributed storage delivery nodes 112A, 112B-112K. For example, if multiple users have uploaded into their directory a song (e.g., "Wish You Were Here" by Pink Floyd), then multiple VFID's corresponding to the respective multiple user songs may be correlated to a single LFID that identifies the common song. This single LFID may then be linked (e.g., via SQL relational database tables) to one or more physical files. For redundancy or access performance reasons, multiple physical files corresponding to the song may be stored in more than one storage server. However, it is not necessary to store a physical file for each user. Multiple users can share access to a single physical file. In this way, the SDN system 200 allows de-duplication of files, thereby saving a considerable amount of storage real estate.

The distributed storage delivery nodes 220 (similar to 112A, 112B-112K in FIG. 1) comprise optional archival file storage (AFS) 222, permanent file storage 224. The distributed storage delivery nodes 220 include physical file storage devices such as one or more hard drives. The AFS 222 may archive files, including compressed versions of files stored on or previously stored on the permanent file storage 224. Each storage delivery node 220 also stores one or more tables (e.g., relational database tables) populated by information indicating where files are stored within the respective storage delivery node. The tables may also be populated with path information for each file stored in the distributed storage delivery node 220, and information correlating each file with a logical file identification value (LFID).

Further to FIG. 2, the storage delivery nodes 220 can also include a cache file system 221, a hierarchical storage system 223 and a management and policy-based file replication system 225. The cache file system may be used to temporarily store data before it is stored in a more permanent type of memory storage system. The hierarchical database may be used to manage how data is stored in a hierarchical fashion. The management and policy-based file replication system may be used for managing how many copies of each file are to be stored and whether copies of the files should be stored on high availability storage or archive storage, for example.

The SDN system 200 can also comprise an account management subsystem 206 that manages accounts for end users 114 and/or customers that have an account to access and use the SDN system 200. A customer may be, without limitation, a content and/or application provider. The account management subsystem 206 can, for example, control who can access certain applications and/or content, track usage, and calculate prices and payment data in accordance with a customer's service level agreement (SLA).

An SLA can be an agreement between one or more users and an SDN system administrator or customer, which provides a client interface application to the one or more users. The SLA specifies a level of service (e.g., quality of services, storage and access rights and preferences, etc.) to be provided to the users.

The transaction warehouse 208 can store archival information regarding transactions performed within the VFS 216, including billing, payment history and file operations. This allows for reporting information to be gathered historically.

The middle tier logic 210 does string validation and pre-packages user-inputted data for entry into the IMFS 204. As data is returned from the IMFS 204, the middle tier logic 210 un-packages it for serialization and presentation to the end users 114. In one embodiment, end users 114 need not issue commands directly to the IMFS 204; rather, end user inputs are parsed and transmitted to the IMFS 204 via the middle tier 210. Data returned from the IMFS 204 may go through this same middle tier logic 210. This provides for additional security and command validation prior to entry into the SDN system 200.

In addition to providing secured access to uploaded files, users of the IMFS 204 may have the option of allowing access to individual virtual folders and files to other users. This is accomplished through the sharing subsystem 212 which can be directly correlated to the VFS 216. In this manner, once a user has sent the IMFS 204 a sharing command, a separate entry is created within the VFS 216 linked to the original record. Creation of the entry in the VFS 216 allows the end users 114 to share the file or folder using a different name for the file or folder, but without duplicating the file or folder. End users 114 see the virtual file or folder, and the VFS 216 provides the connection to the original file of folder. Additionally, access restrictions (by IP, password, and so on) can be added to a shared resource, allowing granular control over whom the user is granting access to. Sharing subsystem 212 may also perform public folder mapping functions and functions related to widget creation for APIs.

Uploaded files are processed into the VFS 216 and LFS 218 via a custom file system command processor service. The command processor service can be performed by command processing servers 214, which can determine the uniqueness of each file and perform transcode services as determined by a controlling SLA. Command processing servers 214 can also be used for processing new plug-ins, format translation, advanced tagging, image manipulation and video transcoding.

The command processing servers 214 can also perform metadata extractions to populate the LFS tables with metadata information as explained in more detail in the context of FIG. 5. In one embodiment, the command processing servers 214 can determine which commands need to be run through a queuing system operating, for example, Microsoft Message Queuing (MSMQ). Further, these queuing system commands can be added to command processing servers 214 without modifying the internal process of the command processing servers 214. The queuing system determines a priority order of each queuing command and balances them across each of the command processing servers 214.

Figure 3:
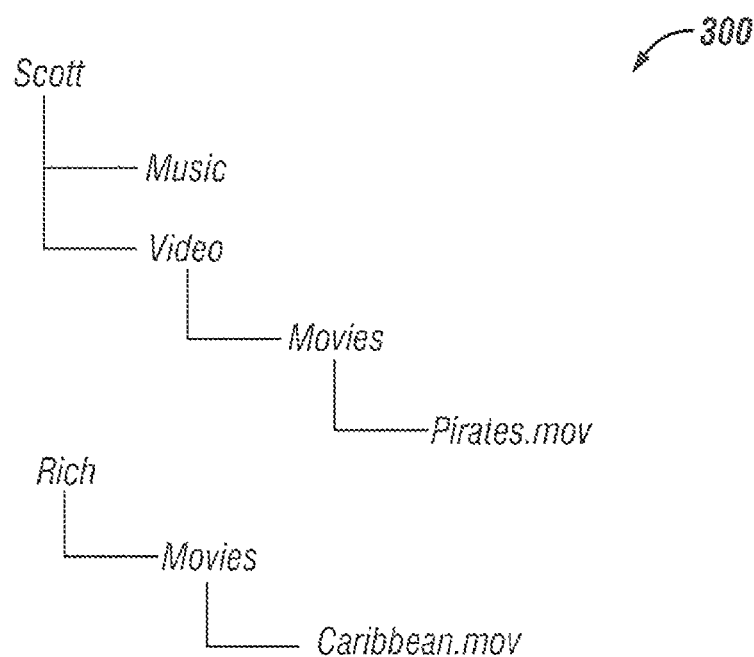
FIG. 3 illustrates exemplary directory structures for folders and files uploaded by two exemplary end users in accordance with one embodiment of the invention.

FIG. 3 illustrates exemplary directory structures 300 for folders and files uploaded by two end users named Scott and Rich. These directory structures 300 may be represented by the following three virtual path names: Scott\music; Scott\video\movies\pirates.mov; and Rich\movies\caribbean.mov.

FIG. 4 illustrates exemplary VFS tables 400 that store user information corresponding to the directory structures and path names of FIG. 3. In one embodiment, the VFS tables 400 comprise SQL relational database tables and include a Virtual Folder Table 4A, a Virtual File Table 4B, and a Virtual Metadata Table 4C. The Virtual Folder Table 4A comprises a "Folder ID" column 402, a "Folder Name" column 404 and a "Parent Folder ID" column 406. As shown in FIG. 4, the Folder ID column 402 contains a unique folder ID value (e.g., values 1-6 in this example) for each user folder that is generated by the VFS 216. The "Folder Name" column 404 contains the name selected by the respective user for each folder (e.g., Scott, Music, etc. in this example). The names in column 404 may be, but need not be, unique. The Parent Folder ID (PFID) column 406 contains the unique Folder ID value of the parent folder of each respective child folder. If the folder is a root folder, its PFID value is null.

The Virtual File Table 4B comprises a "File ID" column 410, a "File Name" column 412, a PFID column 414 and a Logical File ID ("LFID") column 416. The Logical File ID column 416 contains a unique file ID value (e.g., 101) that is generated for each user file, regardless of whether other users may have uploaded that identical file. The File Name column 412 contains the name of the file that is selected by its respective owner/user (e.g., Pirates and Caribbean in the present example). The PFID column 414 is similar to the PFID column 406 discussed above with respect to the Virtual Folder Table 4A. The PFID column 414 contains the Folder ID value 402 of the folder in which the file is stored. For example, the file named "Pirates" has a File ID 12345 and is stored in the folder associated with Folder ID "4" in column 410, which is the folder named "movies." The LFID column 416 contains a value generated for each unique file. If a file is identical with another file, their LFID values may also be identical. Thus, multiple virtual files referencing identical data or content may have a single common LFID value (e.g., 101 in this example). This allows sharing and de-duplication of physical files, thereby reducing the number of physical files that must actually be stored in physical memory.

The Virtual Metadata Table 4C stores metadata that has been created by a respective end user to override pre-existing metadata contained within the original file. In one embodiment, the Virtual Metadata Table 4C contains a File ID column 418 and one or more Metadata Type columns 420. The Metadata Type columns 420 may include columns for image width, image height, video width, video height, video duration, video bit rate, video frame rate, audio title, artist, album, genre, track, bit rate, duration, and other desired information about data or media content. The Virtual Metadata Table 4C allows each user to customize a respective file to a limited extent without affecting whether de-duplication may be appropriate for that particular file. Since the overridden metadata resides only in the VFS 216, only the respective user may access or use that metadata. Furthermore, since the original physical file is not modified, its integrity remains intact and can be de-duplicated if an identical physical file was previously stored in the network.

FIG. 5 illustrates exemplary LFS tables 500, in accordance with one embodiment of the invention. The LFS tables 500 include a Logical File Table 5A, a Logical Node Table 5B, and a Logical Metadata Table 5C. The Logical File Table 5A comprises an LFID column 502, a "Media Key (Hash)" column 504, and a "File Size" column 506. The LFID column 502 stores a unique logical value for each unique file and serves as the linking parameter to the VFS tables 400 discussed above with respect to FIG. 4. The Media Key column 504 stores a unique algorithmically calculated value (e.g., media key or hash) for each unique data file. To illustrate, in the present example Scott's movie named "Pirates" and Rich's movie named "Caribbean" refer to the identical data file containing the movie "Pirates of the Caribbean". Both Scott's movie and Rich's movie will be assigned the same LFID (e.g., 101), because the hash algorithm will generate an identical media key value or hash value. As shown in FIG. 5, one entry in the LFID column is "4", which, as discussed above, indicates a temporary value stored in one or more LFS tables 500. The "−1" entry remains until a media key is calculated by a designated storage node to determine whether the file can be de-duplicated or needs to be physically stored at a designated storage node. The File Size column 506 contains the file size value of the associated physical file.

The Logical Node Table 5B contains an LFID column 508, a Node ID column 510 and an Online column 512. The LFID column 508 links the Logical Node Table 5B with the Logical File Table 5A. The Node ID column 510 associates a unique value assigned to respective storage nodes in the distributed storage delivery nodes 112 with each LFID value. Thus, the Node ID column 510 indicates in which node 112 a physical file associated with an LFID is located. The Online column 512 contains a binary value that indicates whether a corresponding storage node is online or offline. Depending on a user's or customer's service level agreement (SLA), for example, a particular user's physical files may be stored at multiple physical locations for redundancy purposes. The particular user's physical files may also be stored at multiple physical locations to accommodate upload and download performance requirements for a particular application or file. Therefore, the copies of the physical file may be stored in multiple storage nodes. At various times, and for various reasons, one or more of such multiple storage nodes may be offline (e.g., due to hardware failure, down for maintenance, etc.). In the exemplary table, a "1" in the Online column 5B indicates the respective storage node is online and operational and a "0" indicates the corresponding storage node is offline.

The Logical Metadata Table 5C comprises an LFID column 514 which contains the LFID value for each unique logical file in one or more Metadata Type columns 516 that contain the original, intrinsic metadata that was embedded with the original physical file. The Metadata Types can be identical or similar to those discussed above with respect to FIG. 4. If an end user has not over-ridden the original metadata with his or her own custom metadata, the original metadata contained in this table 5C is available as the default metadata to the end user.

Figures 6, 7A:
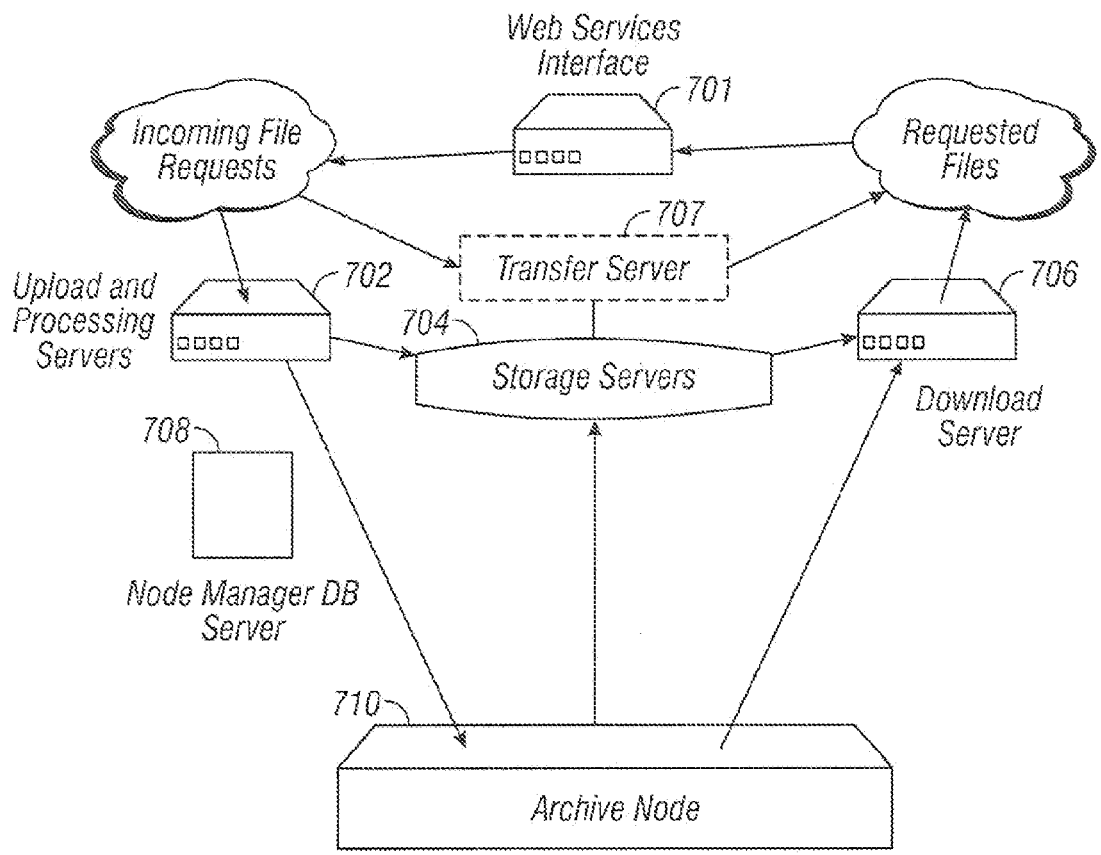
FIG. 6 illustrates an exemplary Physical File Table which is stored in a node manager database server in accordance with one embodiment of the invention.
FIG. 7A illustrates an exemplary storage node architecture in accordance with one embodiment of the invention.

FIG. 6 shows an exemplary Physical File Table 600. Physical File Table 600 table includes an LFID column 602 which is used as a common linking parameter to link back to the VFS and LFS tables 400/500 discussed with reference to FIGS. 4A-4C and 5A-5C. In this manner, Physical file Table 600 links the distributed storage delivery nodes 112A, 112B-112K to the IMFS 108 via the LFID generated by the LFS 107. As discussed above, the LFID column 602 stores a unique identification value for each unique physical file that generates a unique media key value. The Physical Location 604 column stores location or path information that indicates the actual physical location of the file in memory. In FIG. 6, the illustrated path indicates that the file is stored in storage node "ST01" at server "Share1" within the storage node. In addition, the illustrated path indicates further branch names of 7.15, 15.45, and "XYZ47". The branch name of 7.15 refers to the date the file was created. The branch name of 15.45 refers to the time the file was created. The branch name of "XYZ47" refers to an exemplary automatically generated pseudo-name of "XYZ47" generated by the node processing server (e.g., by hashing the original name of the file).

As discussed above, the LFS 218 can store information indicating the storage node or storage nodes in which each file is stored. In accordance with one embodiment, the LFS 218 stores information indicating that the file exists somewhere within a storage node, but does not indicate where the file is located within that storage node. Instead, each storage delivery node 112 can autonomously control the placement of files within itself. Moreover, the Physical File Table stored within each respective storage node contains the information indicating where each files stored within a particular storage node are located within that storage node.

In one embodiment, the VFS tables 400 are stored in a separate database from the LFS tables 500. Both the VFS tables 400 and the LFS tables 500 are separate from Physical File Tables 600, which are stored at respective geographically distributed storage delivery nodes 112. By providing three distinct layers (e.g., the virtual, logical and physical layers) the SDN system 100 de-couples user information from the actual physical files belonging to each of the end users 114. In order to search for and/or utilize information, a hacker would need to infiltrate at least three separate databases and correlate a vast amount of information to determine which file belongs to which user or customer. Furthermore, a hacker would not likely know in advance whether any particular storage node database has any of the physical files a hacker may be interested in. This de-coupling and de-identification of files from users provides added security to sensitive information such as financial and bank account information. The de-coupling and de-identification of files from users features may be used to meet HIPPA requirements for de-identification of patient related information and medical records, for example.

FIG. 7A illustrates an exemplary storage node architecture 700 in accordance with one embodiment of the invention. The storage node architecture 700 includes one or more upload and processing servers 702, one or more transfer servers 707, one or more storage servers 704, a download server 706, a node manager database server 708, and an archive storage node 710. In one embodiment, the archive storage node 710 provides a cheaper form of storage (e.g., magnetic tape) than server storage drives, and stores archive files which do not need to be accessed quickly and/or frequently. In exemplary embodiments, frequently accessed user files are stored in one or more storages nodes having high-availability (HA) storage servers; whereas less frequently accessed files can be stored in separate archive storage nodes. The HA storage servers can be systems with directly attached storage devices. Alternatively, those servers can be attached to network attached storage (NAS) or a storage area network (SAN).

Various server configurations may be implemented in accordance with design requirements and considerations. For example, upload and download functionalities can be performed by transfer server 707 instead of separate servers 702 and 706. In addition, processing functionalities can be implemented by a separate server. Furthermore, node manager database server 708 can control and keep track of where files are stored among the storage servers 704 of storage node 700.

In one embodiment, files can be stored at an archive storage node and copied to a HA storage node when the file is in demand (e.g. being accessed by a user), for example. A file may thereafter be deleted off of the HA storage node when the file is no longer in demand. An ageing algorithm can be used to determine when the file should be deleted from the HA storage. Thus, a copy of a file can be maintained on the archive storage node 710, copied to a HA storage node when the file is in demand (e.g., when a file is frequently accessed), and deleted from the HA storage node when the file is no longer in demand.

Figure 7B:
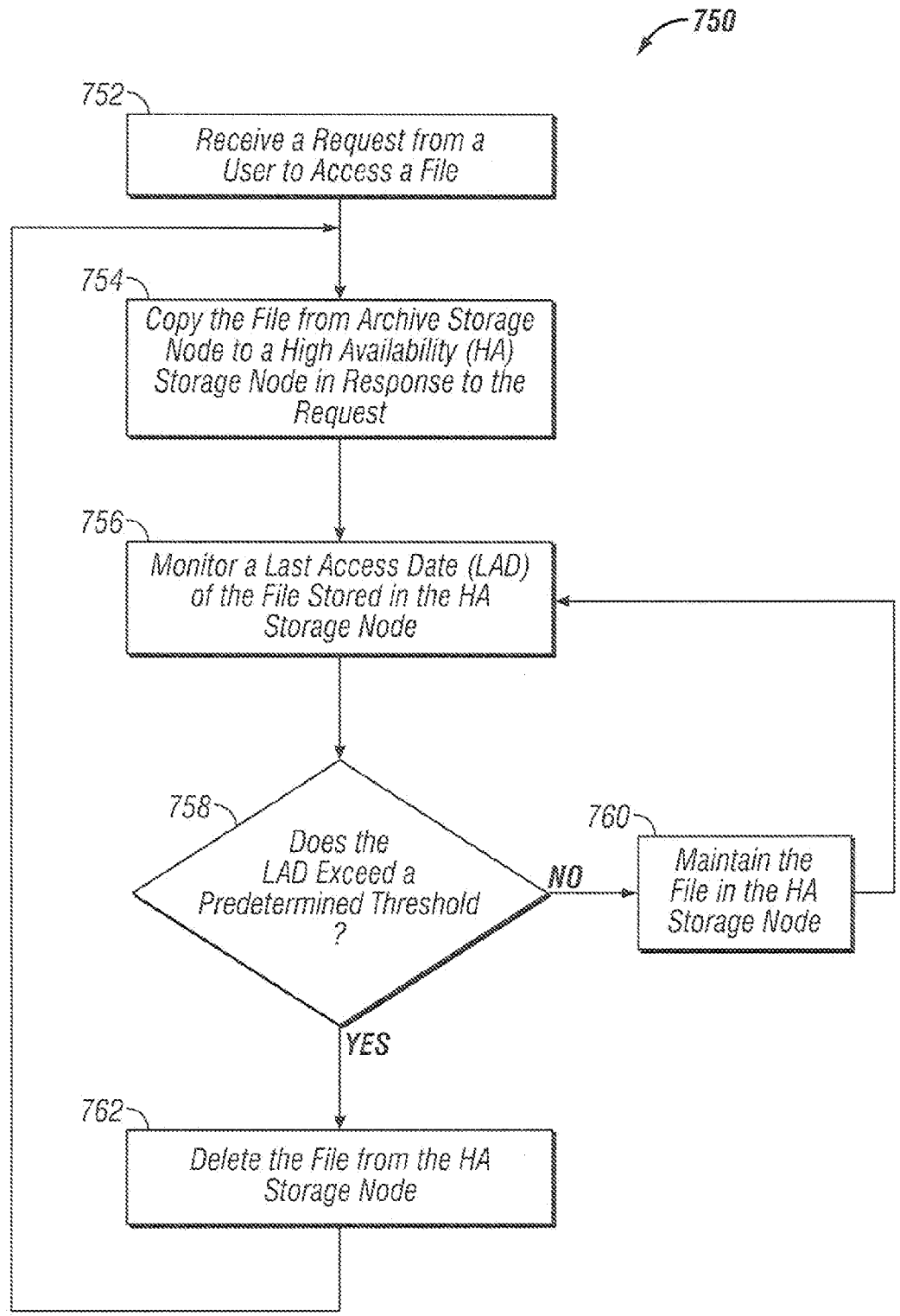
FIG. 7B illustrates a flowchart of an exemplary process for moving requested files from one storage node to another.

FIG. 7B is flowchart illustrating an exemplary process 750 for moving requested files from one storage node to another in accordance with one embodiment of the present invention. The various tasks performed in connection with process 750 may be implemented by software, hardware, firmware, a computer-readable medium storing computer executable instructions for performing the process method, or any combination thereof. It should be appreciated that process 750 may include any number of additional or alternative tasks. The tasks shown in FIG. 7B need not be performed in the illustrated order, and process 750 may be incorporated into a more comprehensive procedure or process having additional functionality not described in detail herein. For illustrative purposes, the following description of process 750 may refer to elements mentioned above in connection with FIGS. 1-7A. In various embodiments, portions of process 750 may be performed by different elements of systems 100-700, such as core system 102, customer application interface 110, and the distributed storage delivery nodes 112A, 112B-112K. Tasks of process 750 may be performed as backend processes that are transparent to the user.

At a step 752, a user requests access to a file stored on an archive node. The requested copy is then copied from the archive storage node to a HA storage node at step 754. A time since last access date (LAD) of file stored on the HA storage node can then be periodically monitored at step 756 to determine if the file is in demand. In this regard, the LAD can be compared to a predetermined threshold at decision step 758. The predetermined threshold can correspond to a predetermined time period, e.g., 30 days. If the LAD exceeds the threshold (Yes branch of decision step 758), then the file is deleted from the HA storage node at step 762. If the LAD does not exceed the threshold (No branch of decision step 758), then the file is maintained on the HA storage node at step 760 and the LAD is periodically monitored again at step 756. If the file is requested after the file has been deleted from the HA storage node, then process 750 may be repeated.

With reference to FIG. 1, when an upload request from an end user 114 is received by the core system 102, the core system 102 can redirect the end user 114 to one of the storage delivery nodes 112A, 112B-112K for uploading the requested file. The end user's connection to the core system 102 is then severed, and a connection is established with the upload server 702 at the storage delivery node 112. The node 112 may then begin accepting data packets of the file from end user 114.

Figure 8A:
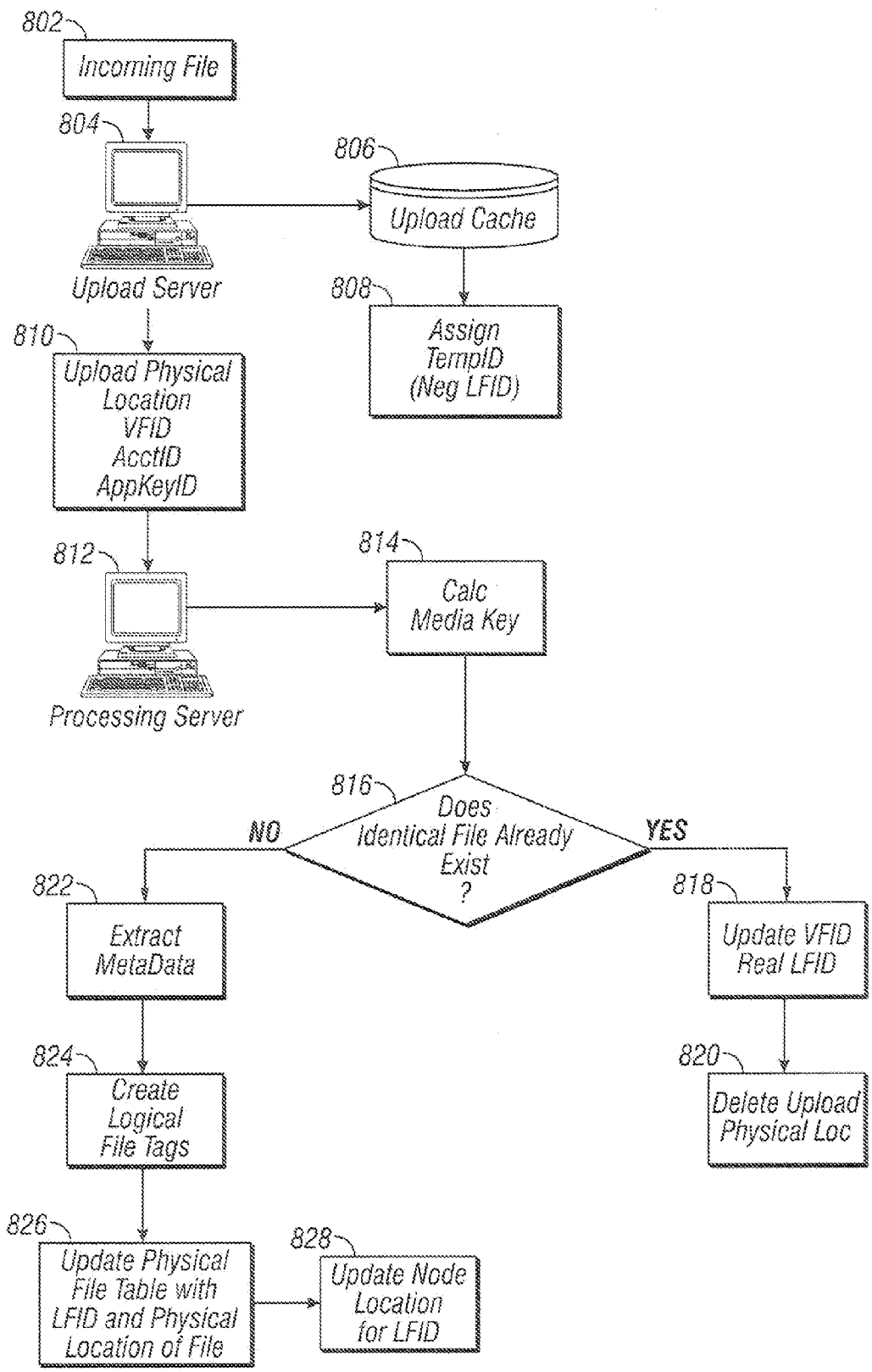
FIG. 8A illustrates a flowchart of an exemplary upload process performed by a designated node in accordance with one embodiment of the present invention.

FIG. 8A is a flowchart of an exemplary file upload process 800 in accordance with one embodiment of the present invention. The various tasks performed in connection with process 800 may be implemented by software, hardware, firmware, a computer-readable medium storing computer executable instructions for performing the process method, or any combination thereof. It should be appreciated that process 800 may include any number of additional or alternative tasks. The tasks shown in FIG. 8A need not be performed in the illustrated order, and process 800 may be incorporated into a more comprehensive procedure or process having additional functionality not described in detail herein. For illustrative purposes, the following description of process 800 may refer to elements mentioned above in connection with FIGS. 1-7. In various embodiments, portions of process 800 may be performed by different elements of systems 100-700, such as core system 102, customer application interface 110, and the distributed storage delivery nodes 112A, 112B-112K. Tasks of process 800 may be performed as backend processes that are transparent to the end user 114.

When an incoming file 802 is received, the upload server 804 stores the file in an upload cache memory 806. The VFS 105 also creates a folder path or virtual file for the end user 114 and assigns a temporary LFID (task 808). The temporary LFID may, for example, be a negative LFID value as discussed with reference to FIG. 5A. The temporary LFID allows the end user to access the newly uploaded file immediately via a download server (e.g., server 706 of FIG. 7). In this manner, the impact of file processing delays on a user's ability to access the file can be decreased or eliminated. The upload server 804 then notifies the node's internal processing server 812 by adding an entry (task 810) into a processing queue. The entry can contain information such as a physical location of the file to be uploaded (e.g., a location of the end user's computer), the VFID associated with the file, an account ID associated with the end user 114, an application key ID, a temporary location of the file, and the like.

With further reference to FIG. 8, processing server 812 applies a hashing algorithm to the uploaded file to calculate a media key for the file (task 814). The hashing algorithm can be the MD5 file hashing algorithm (internet standard RFC 1312), for example. The result from the hashing algorithm can be referred to herein as "hash" or a "media key". Once this media key is created, the processing server 812 may provide a copy of the media key to the LFS 105 (FIG. 1), in accordance with one embodiment of the invention. The LFS 105 may compare the media key to other media keys in its Logical File Tables (FIG. 5A) to determine if an identical media key exists (inquiry 816). An identical media key indicates that an identical file is already stored on the system 100. If an identical file is already stored on the system 100 ("Yes" branch of inquiry task 816), then the temporary LFID is replaced with a permanent or real LFID associated with the previously stored identical file and the end user's VFID is updated with the real LFID (task 818). Since an identical file is already stored on the system, the recently uploaded file can be deleted (task 820).

If the LFS 218 determines that an identical copy of the file is not already stored on the system 200 (No branch of inquiry task 816), then the LFS 218 extracts metadata from the recently uploaded file (task 822) and creates logical file tags (task 824) for storage in a metadata table (FIG. 4C) within the LFS 218. The newly uploaded file may then be assigned a unique LFID, which is stored in LFS 218. The uploaded file is stored in a storage node 112 (FIG. 1) and the Physical File Table stored in a node manager database of the storage node 112 is updated with the LFID associated with the file and a physical location of the file within the node (task 826). The LFS 218 is also updated with a Node ID indicating in which node the file is stored (task 828).

Figure 8B:
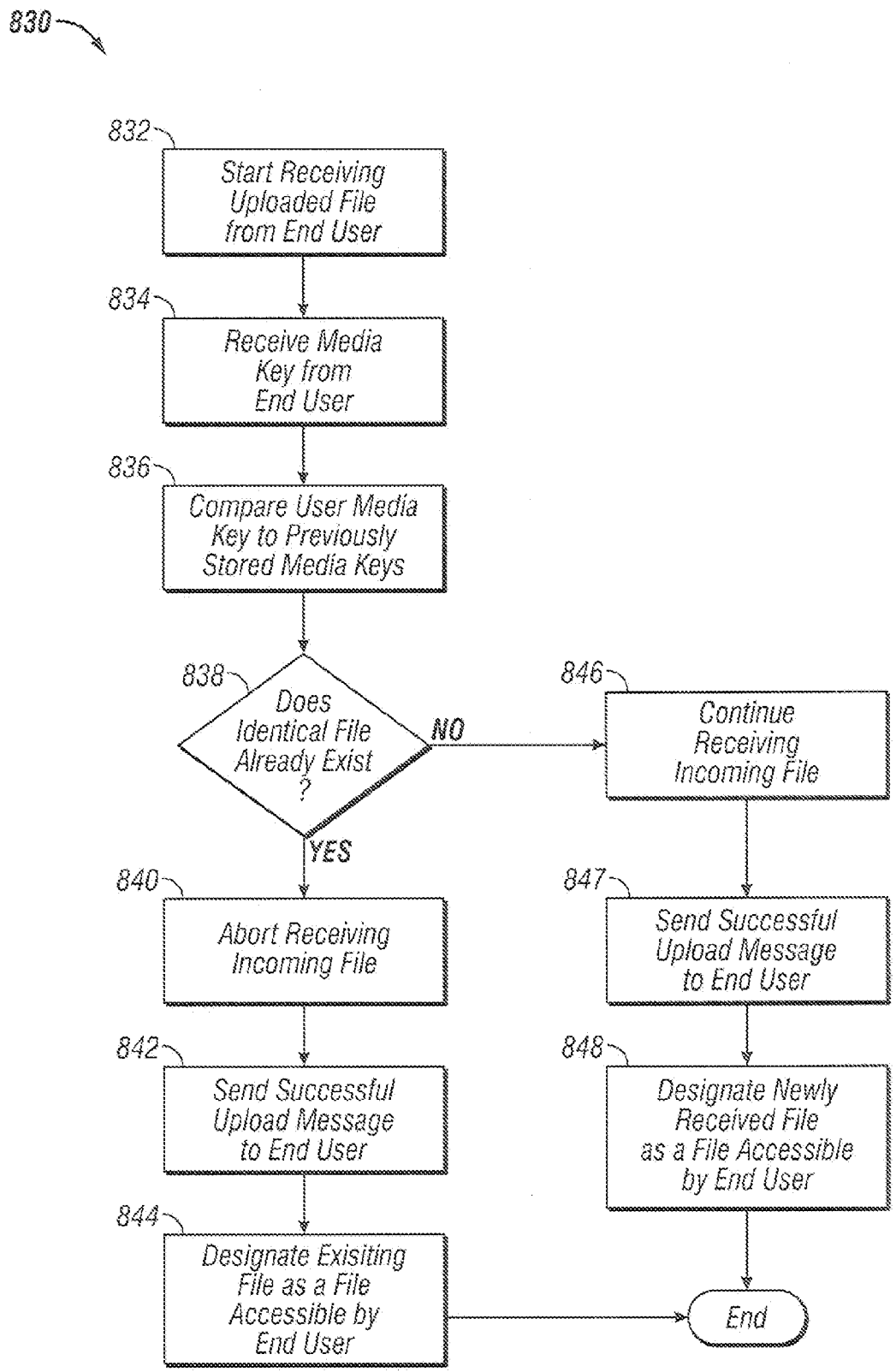
FIG. 8B illustrates an exemplary process for decreasing file upload duration in accordance with one embodiment of the invention.

FIG. 8B illustrates an exemplary process 830 for decreasing file upload duration in accordance with one embodiment of the invention. The various tasks performed in connection with process 830 may be implemented by software, hardware, firmware, a computer-readable medium storing computer executable instructions for performing the process method, or any combination thereof. It should be appreciated that process 830 may include any number of additional or alternative tasks. The tasks shown in FIG. 8B need not be performed in the illustrated order, and process 830 may be incorporated into a more comprehensive procedure or process having additional functionality not described in detail herein. For illustrative purposes, the following description of process 830 may refer to elements mentioned above in connection with FIGS. 1-7A. In various embodiments, portions of process 830 may be performed by different elements of systems 100-700, such as core system 102, customer application interface 110, and the distributed storage delivery nodes 112A, 112B-112K. Tasks of process 830 may be performed as back-end processes that are transparent to the end user 114.

Process 830 may begin when a designated node begins receiving a file from an end user (task 832). In one embodiment, a media key is calculated by a process local to the file being uploaded. This user-side media key is received shortly after or concurrently with receiving the file being uploaded (task 834) and compared to previously generated and stored media keys (task 836). In one embodiment, a periodically updated table containing all the previously generated media keys are stored at each node for comparison with received user media keys. In an alternative embodiment, the previously generated media keys may be stored in the LFS table 500 (FIG. 5) residing in the core system 102. In this embodiment, the designated node may transmit the received user media key to the core system 102 for comparison with previously stored media keys. In one embodiment, a program (e.g., hash algorithm) is downloaded or installed on the end user's computer to generate the user-side media key. The program may be any type of hashing algorithm, for example, as long as it is the identical program used by the core system 102 to calculate the media keys stored in the LFS table 500 or within memory tables in each node. A match between the user-side media key and a previously stored media key indicates an identical file already exists on SDN system 100. In this way, a determination is made as to whether a file identical to the file being received has previously been stored in system 100 (task 838). If a match is found and uploading has not been completed, then the upload can be aborted (task 840) and a "successful upload" message can be immediately sent to the end user (task 842). The file associated with the matched media key already stored on the SDN system 100 can then be designated as a file associated with the end user (task 842). In this manner, unnecessary uploading of a previously existing file is aborted, thereby avoiding storing a duplicate file on the system and decreasing file upload duration. If the match is not found (No branch of inquiry task 838), uploading of the file continues until it is completed (task 846) after which a "successful upload" message is sent to the end user (task 847). Finally, the newly uploaded file is designated as a file that is accessible by the end user (task 848) and stored on the system 100, as described in process 800 of FIG. 8A, for example.

In one embodiment, when a download request (a.k.a., a retrieve or "get" request) is received by the core system 102 (FIG. 1), the core system 102 determines which one or more distributed storage delivery nodes 112 contain the requested file and which of those storage nodes is closest to the end user 114. The end user 114 is redirected to that storage node. The user's connection to the core system 102 may be severed at this point. It can be noted that just because a storage node is closest to the end user 114 does not necessarily mean that the storage node is "near enough" to the user's device. For example, even though a first node may be determined to be "near enough," a customer's SLA can dictate that a second, different node needs to be used to service the end user. Thus, policies in a customer's SLA can override which node is deemed appropriate.

As used herein, an "end user" is an entity that requests uploading and downloading of files from the SDN. A "customer" can be an end user or, in some instances, a content provider that provides services to many end users, and which has a SLA with the core system operator. In one embodiment, policies in a customer's SLA may override some or all intrinsic features of the SDN's storage and file manipulation rules. For example, a customer may choose to store files wholly within the continental United States, dictating that those files must never be shipped overseas. In this scenario, the logic in the SDN will enforce the policy by overriding any conflicting rules, ensuring this customer's files are never transmitted to restricted nodes during load balancing, file protection or file migration activities, for example. Customer's may choose to "lock" their files to a node or series of nodes or within a geographical region. Additionally, customer's may require that only nodes capable of providing a specified quality of service, no wait or queuing; etc., can be used to service requests for the customer or the customer's clients.

Additionally, a customer may also dictate that any file received by the system must immediately be copied to one or more additional nodes, which may or may not be specifically designated. This provides redundancy and security against data loss and/or corruption even in the event of catastrophe, and can improve performance or quality of service to that specific customer. For example, if the customer frequently travels to California, New York and Europe, the customer may dictate that a copy of each of his or her files be stored in a node geographically situated in each of these regions to minimize latency when he or she requests files from any of these regions.

As a further example, a customer's SLA may dictate that certain groups of end users, which subscribe to the customer's services, be designated for service by specific nodes. For example, a group policy may be set for a specific group of users to be served by specified storage nodes managed by the customer. In this way, node access and utilization may be controlled or optimized by the customer with respect to the customer's subscribers, in accordance with various objectives or criteria specified by the customer (e.g., subscriber management, accounting, and/or other customer business objectives).

Thus, policies set forth in a customer's SLA can override or supplement the SDN file allocation and manipulation rules described herein. Some non-exclusive examples of policies that can be specified in a customer's SLA include: always maintain a predetermined number (e.g., 2) of redundant copies of all files associated with the customer in the SDN; only store the customer's files in one or more pre-specified types of nodes or geographic regions; always serve requests associated with the customer's account using the fastest available node; always serve requests associated with the customer's account using the closest available node; requests associated with the customer's account must be served within a maximum latency threshold or satisfy predetermined quality of service criteria; etc. In one embodiment, a customer's SLA is always checked before moving, copying, storing, or providing access to files associated with the customer. In one embodiment, each customer's SLA and policies associated therewith are stored in a database coupled to the core system 102 (FIG. 1). In further embodiments, all or a subset of all customer SLA's may be redundantly stored at designated storage nodes such that the designated storage nodes can notify the core system 102 if a directed action violates one or more policies of a relevant customer's SLA. Upon receiving such notification, the core system 102 can take any remediation measures.

In one embodiment, when a download request is received by the designated node, the node manager database server 708 (FIG. 7) determines which storage server 704 within the storage node 700 houses the file. A transfer server 707 requests the file location from the node manager database server 708 and then requests the file from the identified storage server (e.g., via a "share" request). The identified server then transfers the file to the transfer server 707 which then passes the file to the requesting user (assuming the user has proper access rights). In one embodiment, the user's connection does not "touch" the servers on which their files are stored. Instead, the end user's connection may access files via a web services proxy agent. The web services proxy agent in turn interfaces with a node download server 706 or transfer server 707, but does not interface with the actual storage server 704 in the storage node 700 (FIG. 7).

Figure 8C:
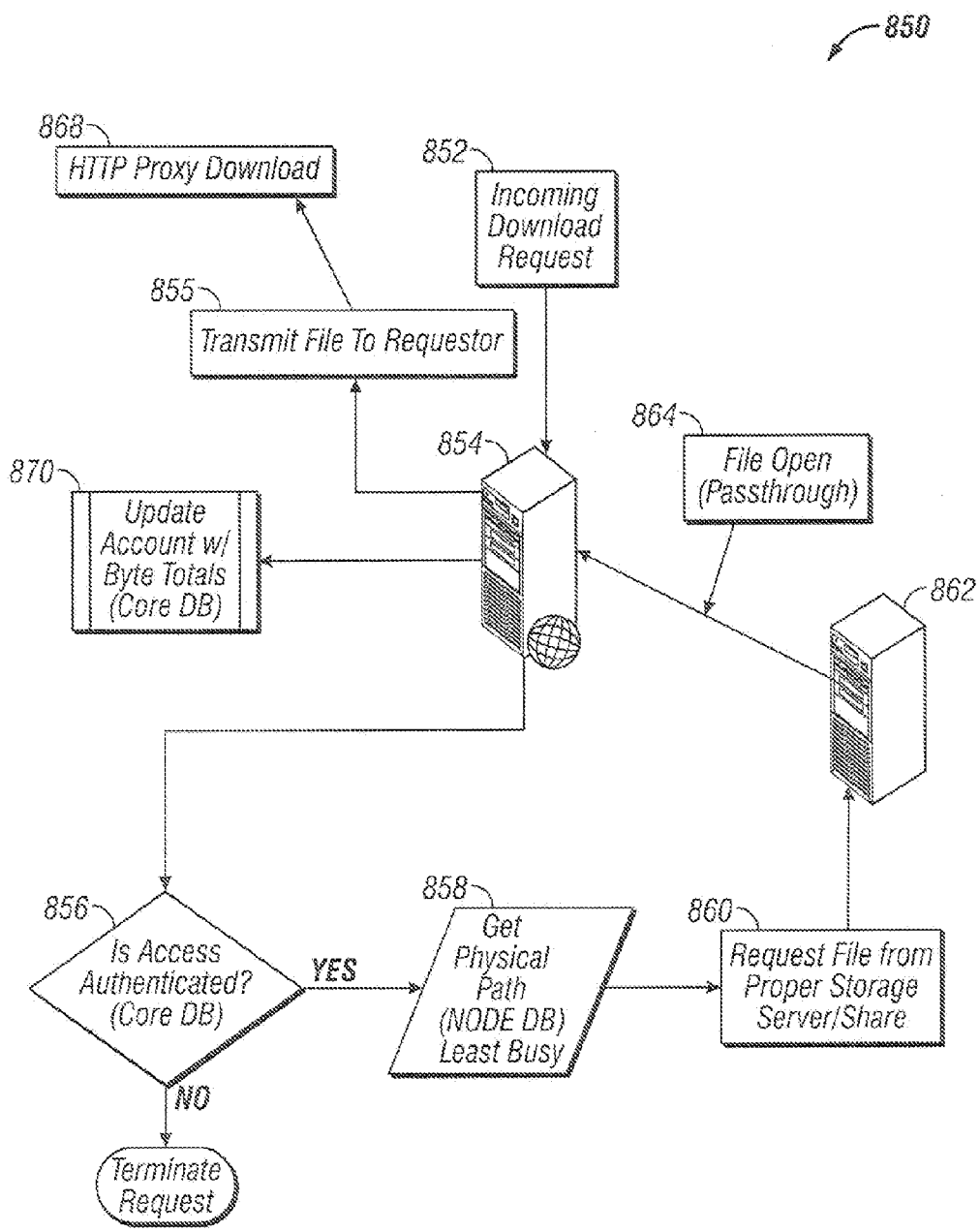
FIG. 8C illustrates a flowchart of an exemplary download process performed in accordance with one embodiment of the present invention.

FIG. 8C illustrates a flowchart of an exemplary download process 850 in accordance with one embodiment of the present invention. The various tasks performed in connection with process 850 may be implemented with software, hardware, firmware, a computer-readable medium storing computer executable instructions for performing the process, or any combination thereof. It should be appreciated that process 850 may include any number of additional or alternative tasks. The tasks shown in FIG. 8C need not be performed in the illustrated order, and process 850 may be incorporated into a more comprehensive procedure or process having additional functionality not described in detail herein. For illustrative purposes, the following description of process 850 may refer to elements mentioned above in connection with FIGS. 1-7. In various embodiments, portions of process 850 may be performed by different elements of systems 100-700, e.g., core system 102, the customer application interface 110, and the distributed storage delivery nodes 112. The tasks of process 850 may be performed as backend processes that are transparent to the end user 114.

It can be noted that process 850 can perform authentication and authorization before actually "serving out the bytes" (i.e., transmitting the file). At the end of each request, process 850 may also record the actual number of bytes served for accounting purposes. If the end user 114 is authenticated and authorized to download the file, then the file's content may be streamed to the requesting client (end user). After the request ends, the actual number of bytes served can be recorded for accounting purposes. This can happen even if the client aborts the download, in which case, the number of bytes served up to that point can be recorded.

At task 852, an incoming download request is received by transfer services server 854. The download request may be a request redirected from core system 102 (FIG. 1) to a storage delivery node 112, for example. A transfer services server 854 can be similar to server 707 of FIG. 7A and be located within the storage delivery node 112. The transfer service server 854 may then communicate with the core system 102 (FIG. 1) for the purpose of authenticating the end user 114 associated with the download request (inquiry task 856). If the end user 114 is not authenticated ("No" branch of the inquiry task 856), then the request is terminated.

If the user is authenticated ("Yes" branch of the inquiry task 856), then the core system 102 determines the identity of a storage node containing the requested file and returns a physical path for that node to the requester's computer (task 858). In one embodiment, if multiple nodes are identified as containing the requested file, the core system 102 selects the node that is closest and/or least busy, or makes its node selection based on some combination of these factors. The physical path for the selected node is correlated with an LFID associated with the user's virtual file path for the requested download file. The local node manager database server 708 at the selected node (FIG. 7A) may further determine the physical location of the file within the node given the LFID (task 858) using Physical File Table 600 (FIG. 6). Once the physical location of the file is determined, the node manager database server 708 then requests the file from the proper storage server 862 (task 860). In one embodiment, the proper storage server is the least busy storage server in the node that contains the requested file. The transfer service server 854 then receives the data packets of the file from the proper storage server 862 and thereafter transmits the file to the requester (task 855). In one embodiment, the file is transferred from the transfer server 854 to the user via a HTTP proxy download program (task 868). The transfer service server 854 may then notify the IMFS 108 of the number of bytes transferred to the user for accounting purposes (task 870).

Figure 8D:
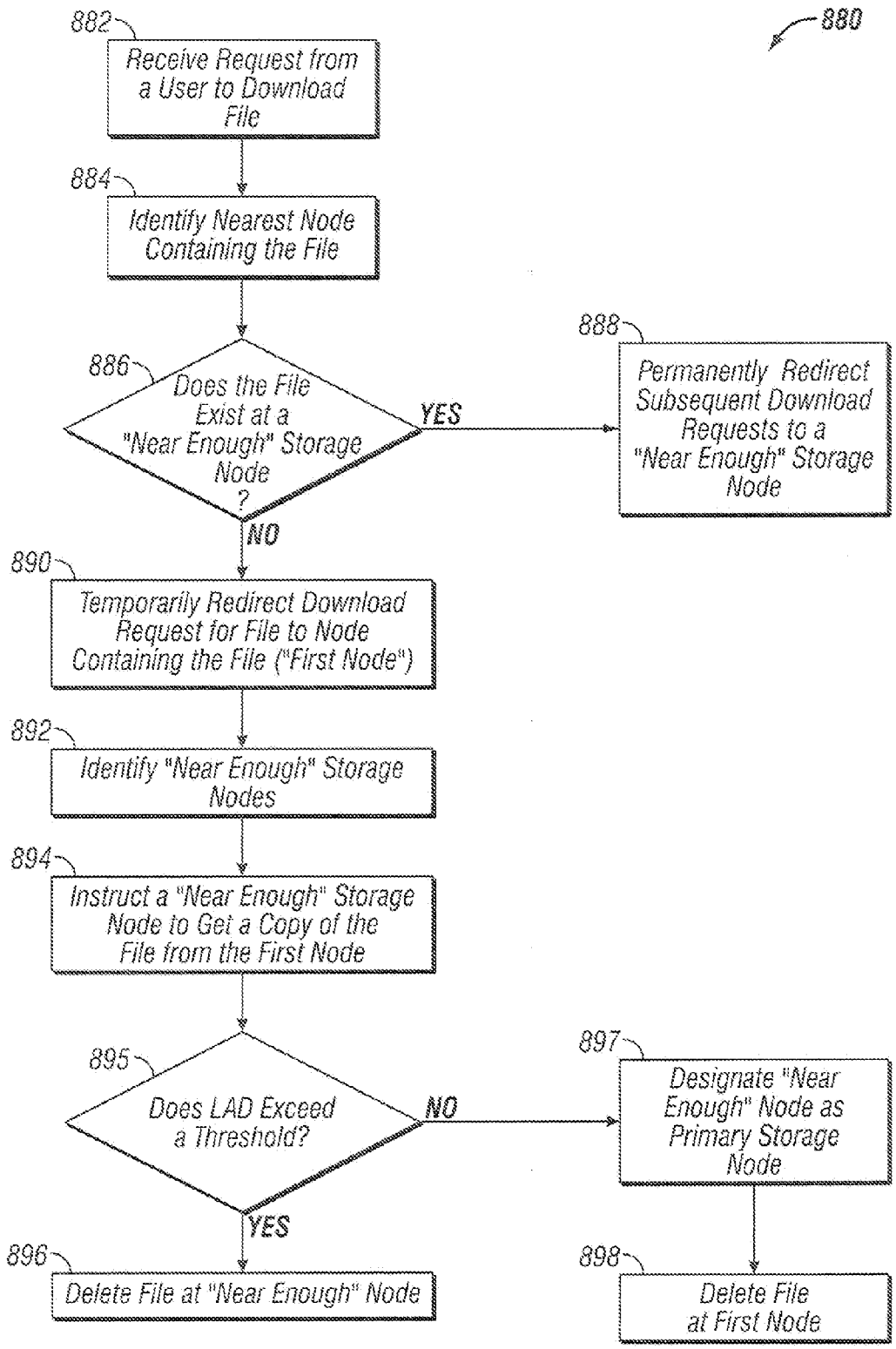
FIG. 8D illustrates an exemplary process for global usage based file location manipulation in accordance with one embodiment of the invention.

FIG. 8D illustrates an exemplary global usage based file location manipulation process 880 in accordance with one embodiment of the invention. The various tasks performed in connection with process 880 may be implemented by software, hardware, firmware, a computer-readable medium storing computer executable instructions for performing the process, or any combination thereof. It should be appreciated that process 880 may include any number of additional or alternative tasks. The tasks shown in FIG. 8D need not be performed in the illustrated order, and process 880 may be incorporated into a more comprehensive procedure or process having additional functionality not described in detail herein. For illustrative purposes, the following description of process 880 may refer to elements mentioned above in connection with FIGS. 1-7A. In various embodiments, portions of process 880 may be performed by different elements of systems 100-700, such as core system 102, customer application interface 110, and the distributed storage delivery nodes 112A, 112B-112K. Tasks of process 880 may be performed as backend processes that are transparent to the end user 114.

Process 880 may begin by receiving a download request at step 882. The download request can be sent from end user 114 and received by core system 102, for example.

The core system 102 then identifies the nearest node containing the requested file in step 884. For example, the core system 102 can determine an LFID associated with the file download request and identify which nodes contain files associated with the LFID using the Logical Node Table described with reference to FIG. 5B. Since copies of a file can be stored in a plurality of nodes, a plurality of nodes may be identified in step 884. As explained in further detail below, in one embodiment, when a plurality of nodes contain copies of the file, a comparison, such as a geocode comparison between the user's geocode and each identified node's geocode may be used to determine which of those nodes is the nearest node or a "near enough" node. Alternatively, a look up table such as a Node Priority Table 1070, described in further detail below, can be accessed to determine which nodes can serve the user based on his or her geocode. Once the available nodes are identified the core system 102 can determine which of those nodes contains the requested file and thereafter redirect the user's request to the highest ranked node for that user's geocode as specified in the Node Priority Table 1070.

The core system 102 can then determine whether the nearest node is a "near enough" node at decision step 886. Just because a node is determined to be nearest to the user in step 884, does not necessarily mean that the node is "near enough." As used herein a "near enough node" can refer to a node that is deemed to be sufficient to process a users request based on various criteria. The criteria can be strictly a distance between the user and a node or can also include additional or alternative factors, such as quality of service a node can provide to the user. The criteria used to determine whether a node is "near enough" can also be specified by an SLA governing the user's request.

If the nearest node is determined to be "near enough", then the core redirects the download requests and all subsequent requests from the user to that node at step 888. Thus, a subsequent request from the user need no longer pass through the core system 102, but instead can directly access the file from the node. In one embodiment, the customer application interface stores the initial download request details, and subsequent requests for the same file by the same IP address are redirected to the previously identified "near enough" storage node.

If none of the nodes containing the file qualify as a "near enough" storage node, then the core system 102 temporarily redirects the user to the nearest node (also referred to as "first node" in this example of FIG. 8D) containing the file at step 890. In other words, the first node serves the download request for the user, but subsequent requests may be directed to a different node.

Next, the core system 102 determines the identity of a "near enough" node at step 892, and instructs the "near enough" node to get a copy of the requested file from the first node at step 894. Accordingly, after step 894, both the first node and the "near enough" node have a copy of the requested file. The core system can then notify the customer application interface of the new "near enough" node's IP address so that subsequent requests for the same file by the same user IP address are directed automatically to the new node identified at step 892.

In a further embodiment, at decision step 894, the core system 102, or a clean up program located at the node, can periodically compare a time since the requested file had been last accessed (LAD) at the "near enough" node with a predetermined threshold. The predetermined threshold can correspond to a period of time, e.g., 10 days. If the LAD exceeds the threshold, then the file at the "near enough" node is deleted in step 896. If the LAD does not exceed the threshold, then the "near enough" node is designated as the primary storage node at step 897 and the copy of the file on the first storage node is deleted at step 898. In this manner, process 880 can move files to nodes which better serve users. Moreover, duplication of files can be reduced by deleting copies of files that are not frequently accessed.

In accordance with various embodiments, a node or other network resource is "near enough" by determining a physical location associated with a user computer by translating its IP address into a geocode and, thereafter, comparing this geocode with a geocode associated with one or more nodes or other network resources. One or more nodes or network resources (e.g., servers) are then assigned to service the user's request (e.g., an upload or download request) based at least in part on the location of the network resource relative to the location of the user's computer as determined by respective geocodes associated with the user's computer and the network resource.

Geocodes are known in the art and used, for example, by the U.S. postal service to assign codes to geographic regions or areas. In general, a geocode is a code that represents a geospatial coordinate measurement of a geographic location and time. A geocode representation can be derived, for example, from the following geospatial attributes: latitude, longitude, altitude, date, local time, global time and other criteria, such as, how the area is coded (e.g., number, letter, mixture of both, or other), which part of the earth is covered (e.g., whole earth, land, water, a continent, a country, etc.), what kind of area or location is being coded (e.g., country, county, airport, etc.), and/or whether an area or point is being coded. Generally, a geocode is a number representation that takes into account some or all of the above criteria.

Every computer or device that communicates over the Internet has a unique Internet Protocol (IP) address assigned to it. Computers and devices residing within a pre-determined geographic region or area are typically assigned a specified range of IP addresses. For example, all computers within Japan may have IP addresses in the range of 43.0.0.0-43.255.255.255 (Source: TANA, Japan Inet, Japan (NET-JAPAN-A).

In one embodiment, when a user or customer makes an upload (a.k.a., "put" or "store") or download (a.k.a., "get" or "retrieve") request, via a web services interface, for example, the request is received by core system 102 which translates the IP address associated with the incoming request into a geocode. The core server 102 looks up a table that correlates IP addresses with geocodes, or IP address ranges with geocode ranges. After the IP address has been translated into a geocode, the system compares the geocode to the geocodes that have been assigned to storage nodes within the network and determines, algorithmically, which resources are "nearest" the requestor. If only one resource is "near enough," the user is redirected to that resource. If multiple resources are "near enough," the system may determine which of the resources is currently experiencing the lightest volume of requests (e.g., via updatable polling) and redirect the requestor to that resource. Or, in an alternative implementation, the requestor may be directed to the absolute nearest resource, regardless of the current volume of requests being handled by that nearest resource.

Figures 9, 10A:
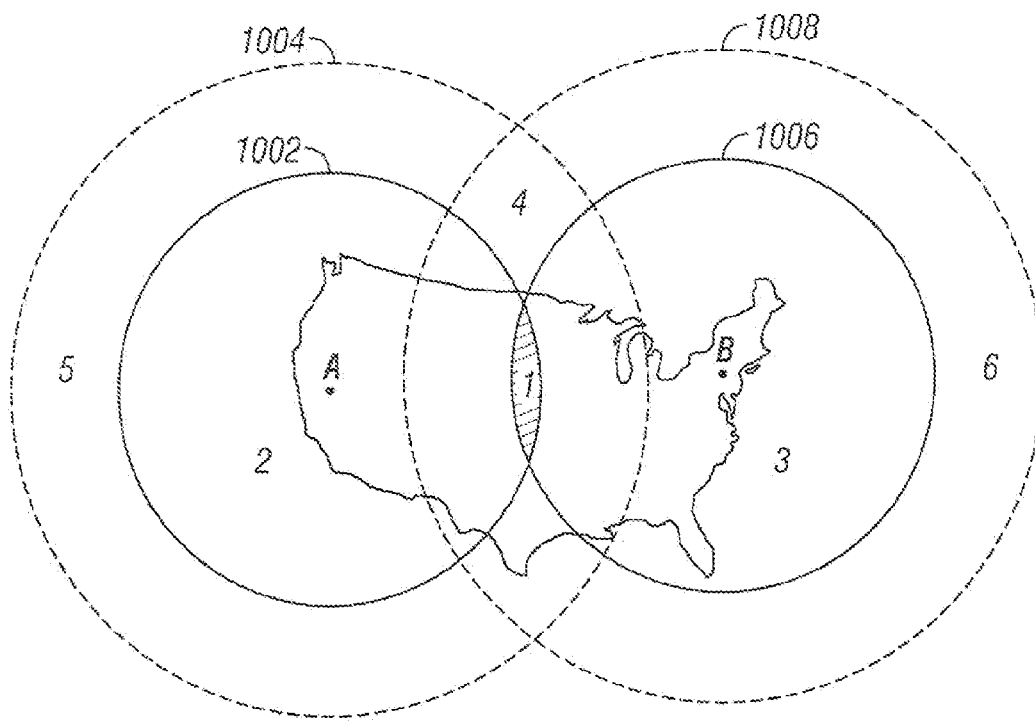
FIG. 9 illustrates an exemplary IP address-to-geocode translation table in accordance with one embodiment of the invention.
FIG. 10A illustrates exemplary geocode regions surrounding two storage nodes in accordance with one embodiment of the invention.

FIG. 9 illustrates an exemplary IP address to Geocode translation table 900, in accordance with one embodiment of the invention. A periodically updated copy of this table 900 may be stored at the core system 102 and at each of the distributed storage delivery nodes 112 within the SDN system 100. As previously discussed above, IP addresses of a group of computers within a particular geographic region or area are typically assigned IP addresses within a range of addresses. FIG. 9 shows some fictional IP addresses 902 and geocodes

904. Generally, IP addresses 902 may include four numerical values separated by a period, similar to that shown in FIG. 9. For example, IP addresses within San Diego county may be assigned an IP address of 192.168.1.X, where X differentiates individual IP addresses within the county. The correlation between IP addresses and geographic areas and regions can be obtained from publicly available sources. For example, third party vendors such as IPLigence may provide such information for a fee. After the IP addresses 902 have been correlated to corresponding geographic areas, this information can then be used to map IP addresses to geocodes 904 based on the correlated geographic information. As previously mentioned, geocodes 904 are known types of codes used by the postal service, for example, to code geographic areas and regions to indicate relative distances and positions between the geographic areas.

In one embodiment, a geocode may comprise at least five numerical fields a-e. As shown in FIG. 9, a first field (a) may indicate a continent (e.g., "7"=Asia), a second field (b) may indicate a country, a third field (c) may indicate a state or region, a fourth field (d) may indicate a city and a fifth field (e) may indicate a postal code, for example. The values of the geocodes are such that a large difference between two geocodes indicates a large distance between the respective geographic regions corresponding to the geocodes. For example, if two geocodes differ in value in the first field of a geocode, then it is known that the corresponding geographic areas are on different continents and quite far from each other. Thus, by storing a geocode for each IP address associated with all users and network resources, relative distances between user devices and network resources can be calculated by calculating the absolute value of the difference between respective geocodes. It is understood that the geocode shown in FIG. 9 is exemplary and other formats and fields may be implemented in accordance with desired criteria and/or applications.

In one embodiment, the core system 102 may determine distances between storage nodes and a user's device, or whether the storage node is "near enough" to the user device, by calculating the absolute value of the difference between the storage node's geocode and the user's geocode. In one embodiment, a storage node is determined to be "near enough" if an absolute value of its corresponding distance is lower than a predetermined threshold value. In further embodiments, additional criteria may be considered to determine whether a node is "near enough," or should be selected to service the user's file request. Such additional factors may include, for example, how busy the node is, as measured by the number of current accesses to the storage node, or number of accesses to a file within a specified time period by a user, bandwidth of the network, speeds of the communication links on the network, quality of service (QoS) of communications on the network, policies and rules as determined by a user's or customer's SLA, master internet trunk information, relative connectivity of the storage nodes within the network, the relative performance capabilities of the node as compared to other nodes, etc. In various embodiments, various combinations of the above factors may be utilized and considered by logic residing in the core system 102 and/or logic within nodes to determine which one of a plurality of nodes should handle the user's request and subsequent requests by the same user.

In an alternative embodiment, the relative distances between nodes and various geographic regions can be used to create a Node Priority Table that prioritizes which nodes have priority with respect to serving end users in each geographic region. In this embodiment, to determine whether a node is "near enough," the core system need not perform any geocode subtractions but simply looks up the Node Priority Table to determine which nodes are designated to serve a particular user request based on a geocode value associated with the user request. A more detailed discussion of a Node Priority Table is provided below with reference to FIG. 10B, in accordance with one embodiment of the invention.

Determining a node to serve a client request will now be described with reference to FIGS. 10A-10D in accordance with various embodiments of the present invention.

FIG. 10A illustrates storage nodes A and B located at separate geographic locations. For example, storage node A may be located in California while storage node B is located in New York. Geocodes 1-6 are assigned to predetermined geographic regions defined by circular boundaries having predetermined radii centered about each node. First and second circular boundaries surrounding node A are defined by circles 1002 and 1004, respectively. Third and fourth circular boundaries surrounding node B are defined by circles 1006 and 1008, respectively. In one embodiment, the boundaries having the smaller radii 1002 and 1006 represents areas that can be considered "closest" to a respective node, and the boundaries having the larger radii 1004 and 1008 can be considered "close enough" to a respective node. Although FIG. 10A illustrates regions defined by circular boundaries, it is appreciated that various shaped boundaries can be used to define geocode regions, such as rectangular shapes. Moreover, geocode regions need not even be defined by particular shapes, but may be defined by other criteria, such as quality of service considerations, latency times, etc. As shown in FIG. 10A, the circles 1002, 1004, 1006 and 1008 define various geographic regions 1-6 with respect to the nodes A and B which may be translated or correlated to geocodes, or geocode regions, in accordance with one embodiment of the invention. A first geocode region 1 corresponds to an area of intersection between circles 1002 and 1004. A second geocode region 2 corresponds to the area within circle 1002 minus region 1. A third geocode region 3 corresponds to the area within circle 1004 minus region 1. Similarly, a fourth geocode region 4 corresponds to an area of intersection between circles 1004 and 1008. A fifth geocode region 5 corresponds to an area within circle 1004 minus regions 2 and 4 and a sixth geocode region 6 corresponds to an area within circle 1008 minus regions 3 and 4.

Figures 10B, 10C:
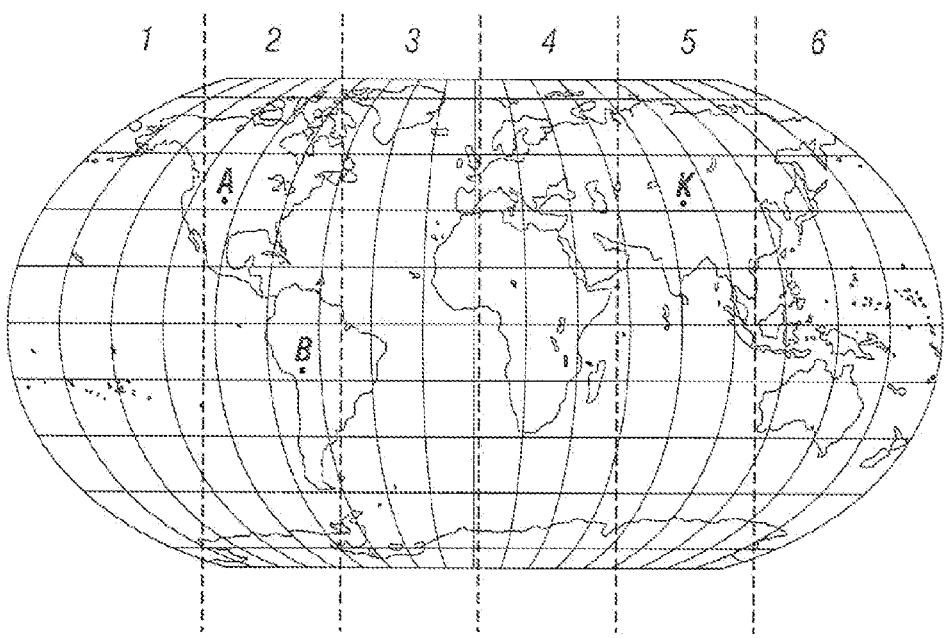
FIG. 10B illustrates an exemplary node priority table in accordance with one embodiment of the invention.
FIG. 10C illustrates exemplary geocode regions based on longitude coordinates in accordance with one embodiment of the invention.

FIG. 10B illustrates a Node Priority Table 1070 associated with the geographic regions of FIG. 10A, in accordance with one exemplary embodiment of the invention. The Node Priority Table 1070 identifies a priority order for a plurality of nodes to which core system 102 may send user requests based on which geocode region (e.g., 1-6) a user is calling from. The Node Priority Table 1070 includes a Geocode ID column 1072, a Priority ID column 1074, and a Node ID column 1076. The Geocode ID column 1072 is populated by the geocode region IDs (e.g., 1-6) of FIG. 10A. The Priority ID column 1074 is populated by values indicating a node access priority associated with each node in each geocode region. The Node ID column 1076 is populated by values identifying a storage node, e.g., A or B which has been designated to service various geocode regions in accordance with a predetermined priority order of selection. Based upon which geocode region an end user 114 is calling from, a particular node can be determined to be a "near enough" or a closest node to the end user 114 using the Node Priority Table 1070. In one embodiment, the Node Priority Table 1070 is stored in the core database server 102 which uses the table to select one or more available nodes to which a user's file request is redirected.

By prioritizing nodes with respect to different geographic regions various algorithms may be implemented to select particular nodes to service user requests originating from various geographic regions. In this example, geographic proximity is a primary factor in determining node selection for a particular user request. However, as would be apparent to those of skill in the art, various additional factors such as server latencies, server performance, quality of service, how busy one node is when compared to another node, etc. may be taken into account and implemented in the node priority table and/or algorithms for selecting nodes to service user requests. In the present example geocode regions shown in FIG. 10A, a geocode ID region that falls within a "closest" radius from a node may be assigned a "1" priority with respect to that node (i.e., a highest priority value). Moreover, a geocode ID region that is outside the "closest" radius, but falls within the "close enough" radius of a node may be assigned a priority "2" region with respect to that node. Regions falling outside of the "near enough" radius may be assigned a priority "3" region.

Thus, as shown in FIG. 10B, geocode ID regions 1 and 2 are considered "closest" to node A. Accordingly, Node Priority Table 1070 has priority "1" values assigned under the Priority ID column 1074 associated with node A in geocode ID regions 1 and 2. Geocode ID regions 4 and 6 fall outside of the "closest" radius, but fall within the "near enough radius." Accordingly, Node Priority Table 1070 has priority "2" values assigned under the Priority ID column 1074 associated with node A in geocode ID regions 4 and 6. Geocode ID region 5 falls outside of the "near enough" radius of node A, and therefore is assigned a priority "3" value under the Priority ID column 1074 associated with node A. The priority IDs are assigned in a similar fashion for node B. Note that some geocodes can have the same Priority ID values for both nodes. In such cases, the node selected to direct a request to can be determined based on various factors, such as which node is less busy or other performance-based factors.

It is understood that geocode regions may be defined in any desired manner to achieve desired performance goals. For example, geocode regions may be defined by longitudinal boundaries in accordance with one embodiment. FIG. 10C illustrates exemplary distributed storage nodes A and B and K located at geographically separate locations around the world. The world is divided into exemplary geocode ID regions 1-6 based on longitudinal boundaries indicated by dashed lines. In the embodiment of FIG. 10C, a geographic area is divided based upon longitudinal boundaries, but it is appreciated that the geographic areas can be divided using zip codes, country codes, and the like. A Node Priority Table can then have a priority ID value for each geocode region 1-6 assigned to some or all of the nodes A, B and K. The priority value can be based on various criteria, including distance from a node to the geocode region and connectivity performance between the geocode region and the node, for example.

Figure 10D:
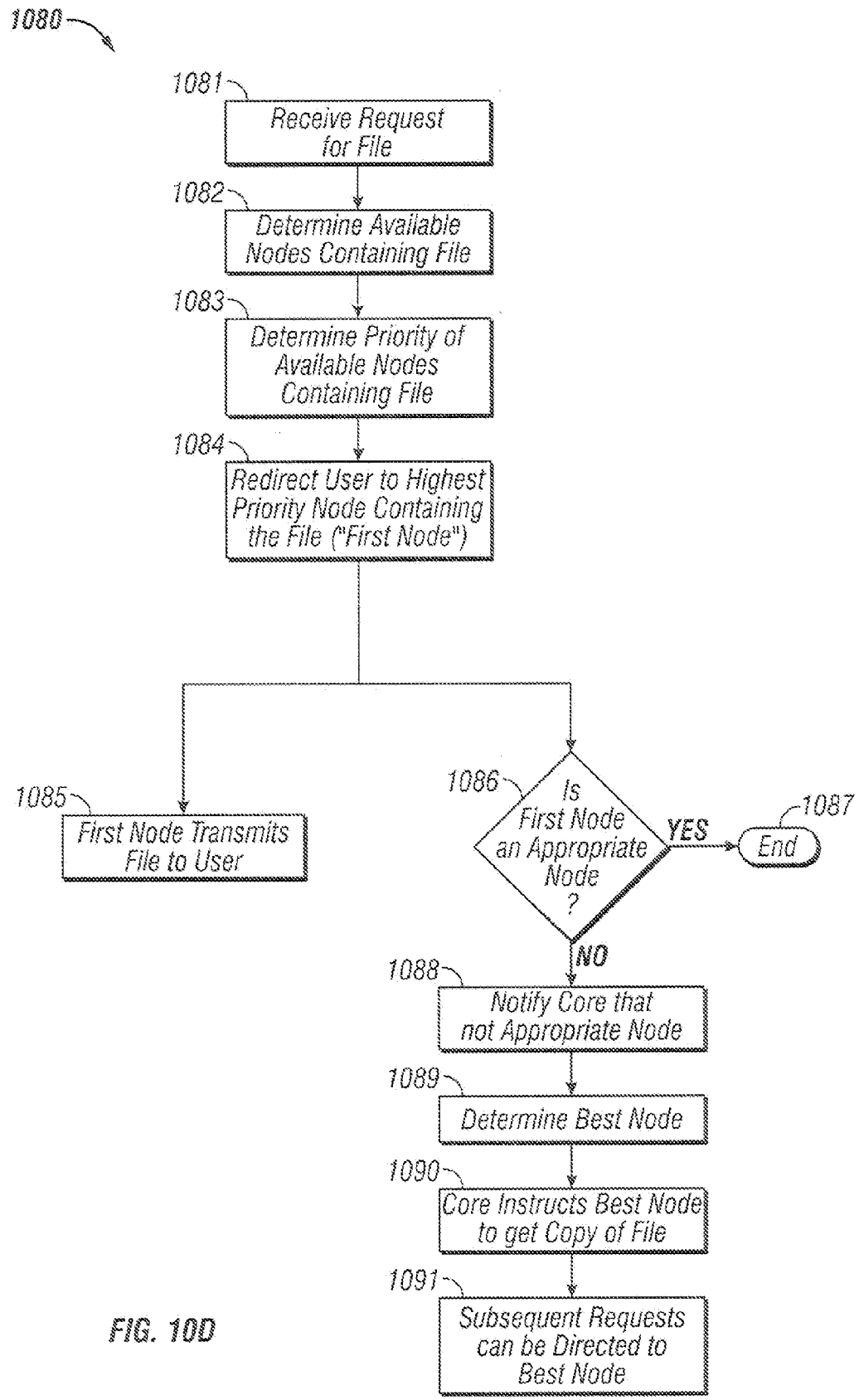
FIG. 10D illustrates a flowchart of an exemplary file location manipulation process in accordance with one embodiment of the invention

FIG. 10D illustrates an exemplary node selection process 1080. The various tasks performed in connection with process 1080 may be implemented by software, hardware, firmware, a computer-readable medium storing computer executable instructions for performing the process method, or any combination thereof. It should be appreciated that process 1080 may include any number of additional or alternative tasks. The tasks shown in FIG. 10D need not be performed in the illustrated order, and process 1080 may be incorporated into a more comprehensive procedure or process having additional functionality not described in detail herein. For illustrative purposes, the following description of process 1080 may refer to elements mentioned above in connection with FIGS. 1-7A. In various embodiments, portions of process 1080 may be performed by different elements of systems 100-700, such as core system 102, customer application interface 110, and the distributed storage delivery nodes 112A, 112B-112K. Tasks of process 1080 may be performed as backend processes that are transparent to the end user 114

For illustrative purposes the following discussion describes a user download request. It is appreciated that process 1080 may be equally applicable to a file upload request with minor modifications. At step 1081, a user request to download a file is received by the core system 102. In one embodiment, the user request includes an IP address of the user's device and a virtual path name of the file being requested.

Next, at step 1082, the core system 102 determines available nodes that contain the requested file. This step is performed by correlating the virtual path name with a LFID as described above with reference to FIGS. 4A-5A. The LFID can then be used to identify which nodes contain the file and which of those nodes are available (e.g., online) using the Logical Node Table of FIG. 5B.

The core system 102 then determines a priority of the available nodes that contain the file in step 1083. This is done correlating the available nodes that contain the file with the Node Priority list 1070 (FIG. 10B) and the geocode ID associated with the region from which the user is calling. The available node that contains the file having the lowest Node Priority ID value is determined to be the highest priority node. Thus, a node having a priority ID value of "1" is determined to be a top priority node, etc.

In step 1084, the user is redirected to the available node that contains the file and is assigned the highest node priority ID. For the purposes of this example, this node can be referred to as the "first node"). The first node then transmits the requested file to the user in step 1085.

Synchronously or asynchronously with transmitting the file to the user in step 1085, the first node determines if it is an appropriate node at decision step 1086. In one embodiment, the first node determines if it is an appropriate node based on whether the users IP address or address range, which the first node obtained from the user, is on a serve list contained in the first node. If the user's IP address is not on the serve list, then the first node is not an appropriate node. In other embodiments, this determination need not be based on a user's IP address, but can instead be based on various criteria, including the user's geocode.

If the first node is determined to be an appropriate node, then process 1080 may end at step 1087.

If the first node determines that it is not an appropriate node, then it notifies the core system 102 that it is not an appropriate node in step 1088. The core system 102 then determines a "best node" to serve further download requests from that user in step 1089. The "best node" can be determined based on various criteria including policies set forth in a controlling SLA. As an example, a controlling SLA may specify a particular node, in which case that node would be considered the best node. As another example, the controlling SLA may specify that the best node is any node that can best serve the user if that node has a copy of the file. In various embodiments, the determination of which node can best serve users can be based on, for example, usage patterns of the various nodes, geographic proximity of the various nodes to a user, latency measures, quality of service requirements for the user as specified in the user's SLA, for example, etc.

Next, the core system 102 instructs the best node to get a copy of the file in step 1090. Subsequent requests for the file can then be directed to the best node in step 1091. It is appreciated that one benefit of the above process is that the node off-loads processing requirements from the core server 102 by determining whether it is an appropriate node to service a user request (step 1086). As mentioned above, this determination can be based on a variety of predetermined criteria (e.g., whether the IP address of the user is on a "serve list," latency considerations, distance considerations, quality of service associated with the request, etc.). In most instances it is contemplated that the selected node will be an appropriate or acceptable node to process a request and, therefore, the node will not need to bother the core server. Only in rare instances will the node notify the core that it is not an appropriate or acceptable node to service a particular request. In this way, the core server 102 does not need to perform an inquiry for every request that is transmitted to it concerning whether a selected node is an appropriate or acceptable node. It simply, redirects a request to a nearest available node containing the requested file and thereafter assumes the node will handle the request. The core server 102 is only notified if there is a problem and thereafter takes appropriate action.

Figure 11A:
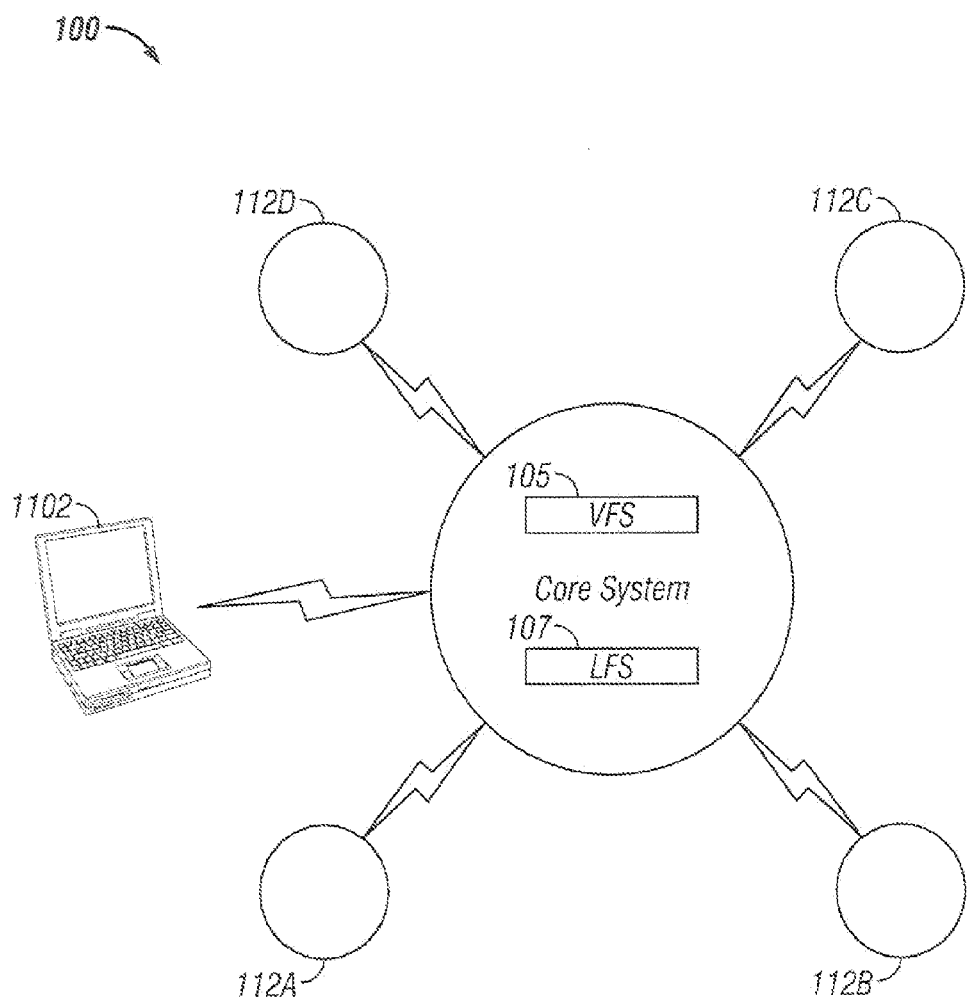
FIG. 11A illustrates an exemplary environment where an exemplary inter-node load balancing process can be performed in accordance with one embodiment of the invention.

An exemplary environment in which an inter-node balancing process may be implemented is described with reference to FIG. 11A below, in accordance with one embodiment of the invention. As shown in FIG. 11A, SDN system 100 includes a core system 102 communicatively coupled to four distributed storage delivery nodes 112A, 112B, 112C and 112D. For the purposes of this example, end user device 1102 is calling from a location closest to storage delivery node 112A and a governing SLA dictates that files requested by the end user device 1102 be moved to a storage node located "closest" to the end user device 1102 at storage delivery node 112A.

As used herein, the term "closest" does not necessarily mean the node is the closest node in terms of absolute distance. The term can also be used to refer to a node that is better suited for connection with the end user because, for example, the connection between the user and the node will result in better performance (e.g., higher data transmission rate) versus another node. Furthermore, a "closest" node may, in fact, be further away than another node, yet still be determined to be a "closest" node due to design efficiencies, and/or relative performance capabilities of the various nodes, and/or the relative load (e.g., number of requests being handled) of the various nodes. Such design efficiencies and/or operation parameters may take into account the ease of managing which nodes users can access as opposed to requiring a strict absolute distance based analysis.

Figure 11B:
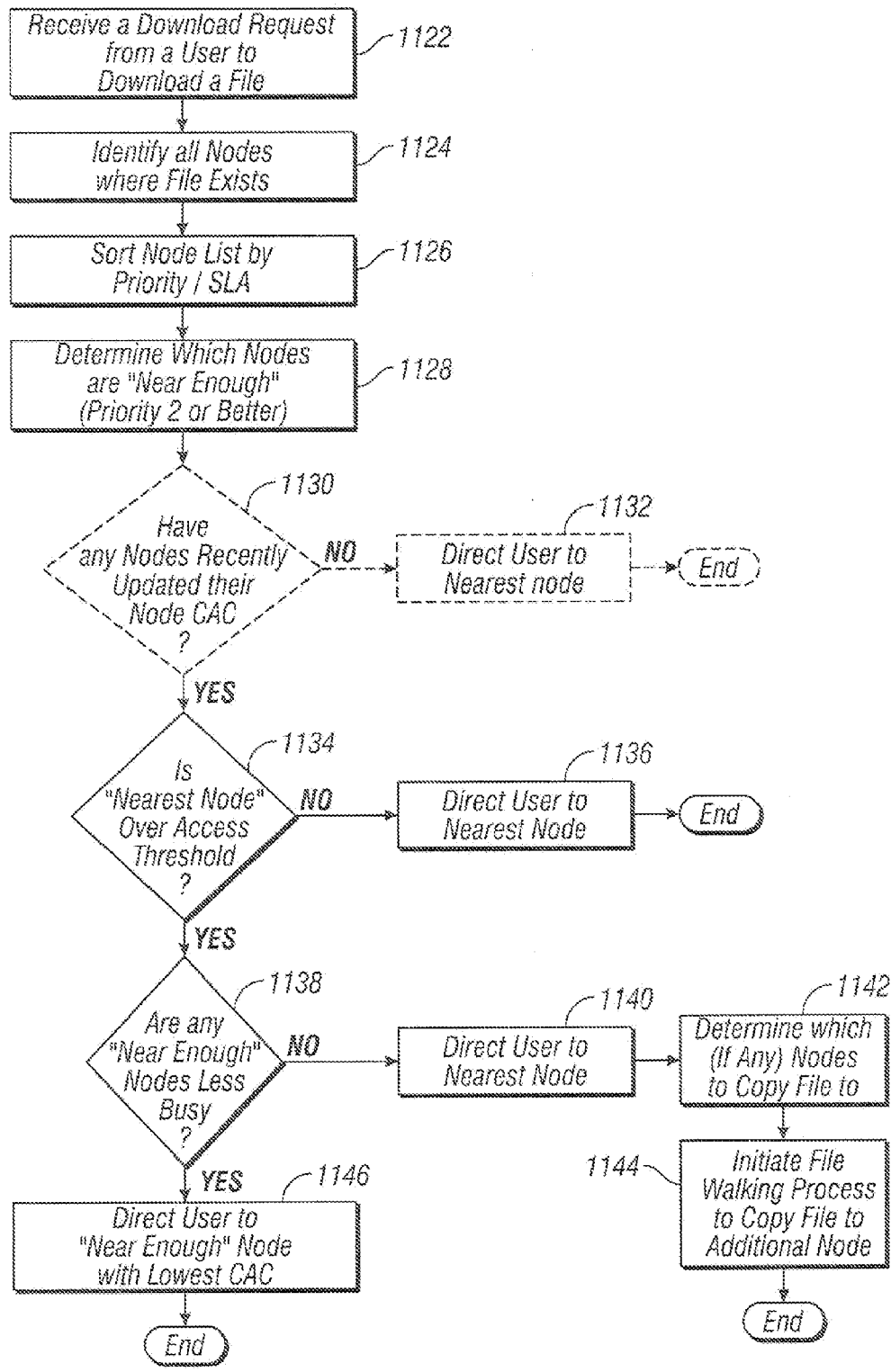
FIG. 11B illustrates a flowchart of an exemplary inter-node load balancing process performed at the core system in the exemplary environment of FIG. 11A in accordance with one embodiment of the invention.

FIG. 11B illustrates a flowchart of an exemplary inter-node load balancing process 1120 that can be performed in the environment of FIG. 11A in accordance with one embodiment of the invention. The various tasks performed in connection with process 1120 may be implemented by software, hardware, firmware, a computer-readable medium storing computer executable instructions for performing the process method, or any combination thereof. It should be appreciated that process 1120 may include any number of additional or alternative tasks. The tasks shown in FIG. 11B need not be performed in the illustrated order, and process 1120 may be incorporated into a more comprehensive procedure or process having additional functionality not described in detail herein. For illustrative purposes, the following description of process 1120 may refer to elements mentioned above in connection with FIGS. 1-11A. In various embodiments, portions of process 1120 may be performed by different elements of systems 100-1100, such as core system 102, customer application interface 110, and the distributed storage delivery nodes 112A, 112B-112K. Tasks of process 1150 may be performed as backend processes that are transparent to the end user 114.

Process 1120 may begin by an end user calling (via the end user device 1102) into the core system 102 and requesting a file (task 1122). The request can comprise the end user's IP address and information corresponding to a virtual path of the requested file. The virtual path name is described in more detail with reference to FIGS. 3 and 4. The core system 102 then translates the virtual path name to its corresponding LFID using tables stored in VFS 105 and LFS 107 (FIG. 1). Thereafter, the core system 102 identifies all the storage nodes in which the file is stored using LFS 107 (task 1124). Next, the identified storage nodes are prioritized by sorting the Node Priority Table 1070 (FIG. 10B) and taking into account the user's SLA (task 1126). The core then determines which of the sorted nodes are "near enough" (e.g., priority 2 or better) (task 1128). Optionally, the core 102 determines whether any of the identified "near enough" nodes have recently updated its current access count (CAC), which is the number of requests a node is currently handling (task 1130). If the answer to inquiry 1130 is "no," then the core 102 directs the user request to the nearest of the near enough nodes (task 1132), after which process 1120 ends.

If the answer to inquiry 1130 is "yes," then the core server 102 determines whether the nearest of the near enough nodes is too busy (i.e., CAC over threshold?) (task 1134). It is appreciated that tasks 1130 and 1132 are optionally implemented by the core in order to potentially bypass tasks 1134-1146, thereby saving processing bandwidth at the core 102, in accordance with one embodiment of the invention. If optional tasks 1130 and 1132 are omitted, then inquiry task 1134 immediately succeeds task 1128 in process 1120. If the answer to inquiry 1134 is "no," then the core 102 directs the user request to the nearest node (task 1136) and process 1120 ends. If the answer to inquiry 1134 is "yes," the core inquires whether any of the other "near enough" nodes are less busy (task 1138). If the answer to inquiry 1138 is "no," then the core 102 directs the user request to the previously identified nearest node (task 1140) where it is queued for handling. Next, the core determines if there is another near enough node to copy the file to (task 1142). If so, the core initiates a "file walking" process by instructing the new "near enough" node to copy the file from one of the previously identified nodes containing the file (task 1144).

If the answer to inquiry 1138 is "yes," the core 102 directs the user request to the "near enough" node with the lowest current access count (CAC) (task 1146). If there is only one "near enough" node containing the file that is less busy than the nearest node, then the user request is automatically directed to that "near enough" node.

Figure 11C:
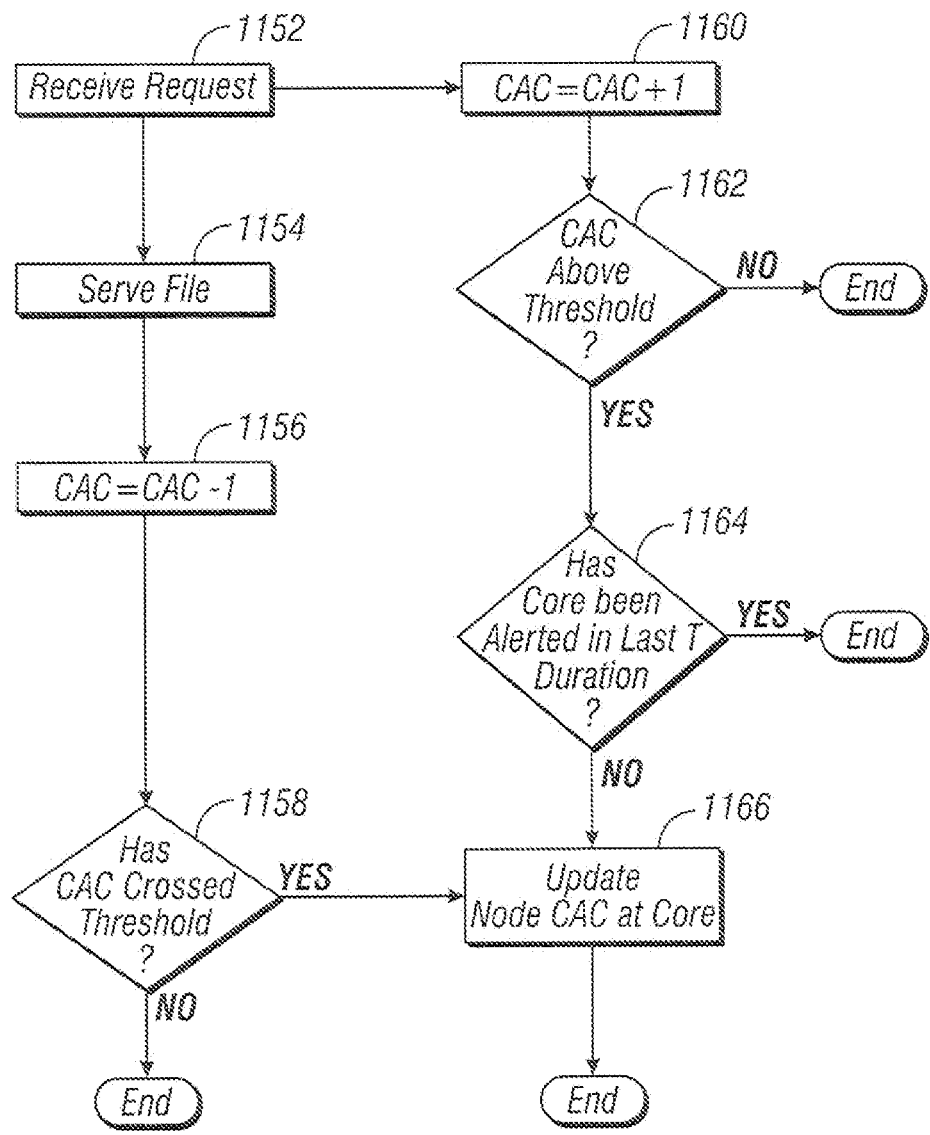
FIG. 11C illustrates a flowchart of an exemplary inter-node load balancing process performed at a storage node in the exemplary environment of FIG. 11A in accordance with one embodiment of the invention.

FIG. 11C illustrates a supplemental inter-node balancing process 1150 which is implemented by a storage node, in accordance with one embodiment of the invention. Whenever the user's request is redirected to a storage node (e.g., tasks 1132, 1136, 1140 or 1146 of FIG. 11B), the storage node will receive the user's request (task 1152) and thereafter serve the file to the end user (task 1154). After completing the transfer of the file to the user, the node decrements its current access count (CAC) by 1 (task 1156) and then determines whether its CAC has crossed a threshold indicating that the node is no longer "too busy" (inquiry task 1158). If the answer to inquiry 1158 is "no," then there has not been a change of status of the node and the process 1150 ends. If the answer to inquiry 1158 is "yes," this means that the node was previously "too busy" but is no longer "too busy." Therefore, the node notifies the core 102 that it is no longer "too busy" by updating the core 102 with its node CAC value (task 1166).

Immediately upon receiving a request from a user, the node increments its CAC by 1 (task 1160). Next, concurrently with processing the user request, the node determines whether its CAC value is above a predetermined threshold value (e.g., 100 requests) (task 1162). If the answer to inquiry 1162 is "no," then the node is not "too busy" and the node need not notify the core. If the answer to inquiry 1162 is "yes," then the node determines whether the core 102 was previously notified of its "too busy" status within a predetermined duration of time T (task 1164). If the answer to inquiry 1164 is "yes," then the core 102 already knows of the current "too busy" status of the node and no further notification is needed. If the answer to inquiry 1164 is "no," then the node notifies the core 102 that it is "too busy" by updating the core 102 with its CAC value (task 1166). Thus, in this embodiment, the node notifies the core when its status changes from "too busy" to "not too busy" and further notifies the core if its status is "too busy" and the core has not been alerted of its "too busy" status within a predetermined time period.

Figure 11D:
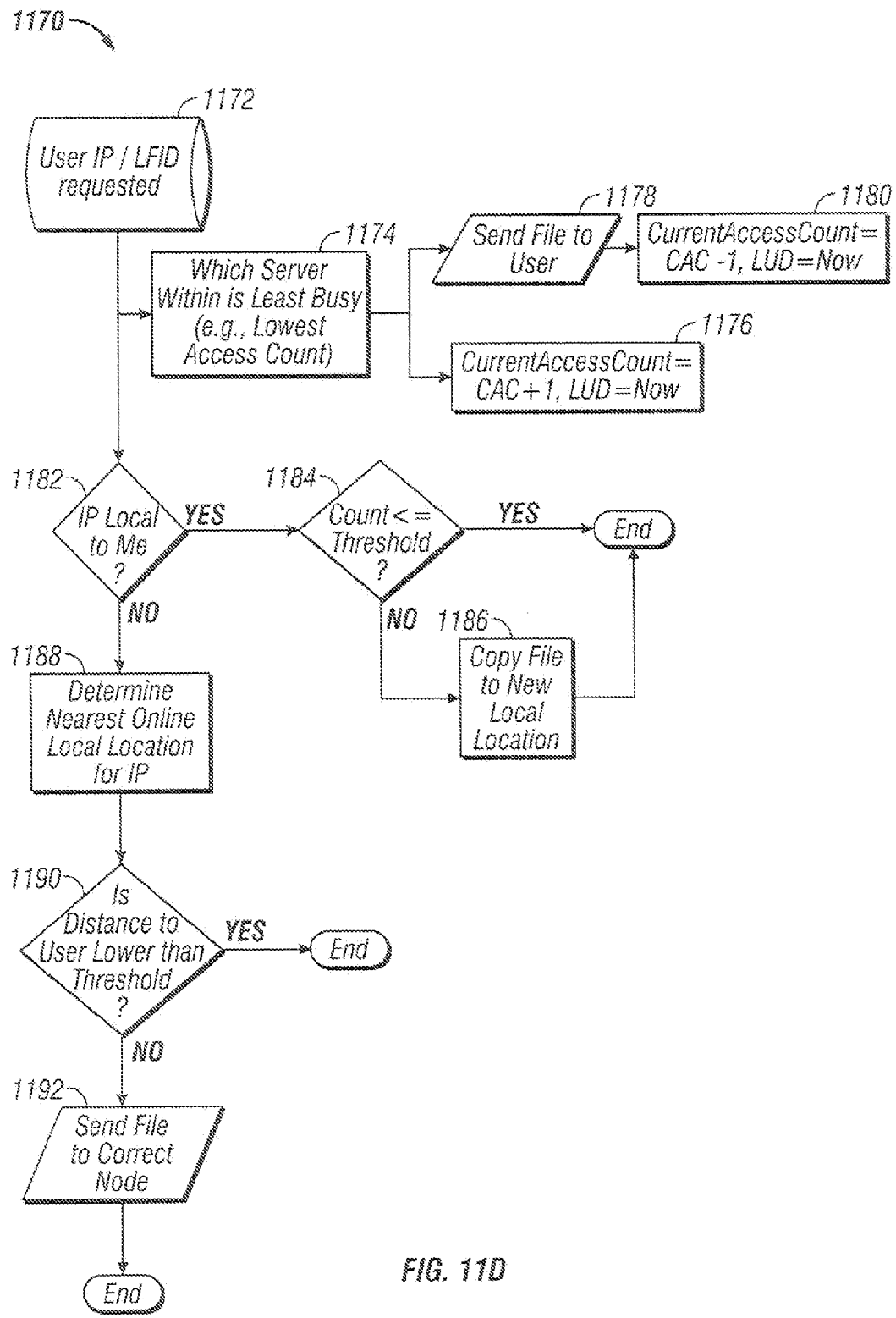
FIG. 11D illustrates a flowchart of an exemplary intra-node load balancing combined with an inter-node load balancing process in accordance with one embodiment of the invention.

FIG. 11D is an exemplary intra-node load combined with an inter-node load balancing process 1170 in accordance with one embodiment of the present invention. The various tasks performed in connection with process 1170 may be implemented by software, hardware, firmware, a computer-readable medium storing computer executable instructions for performing the process method, or any combination thereof. It should be appreciated that process 1170 may include any number of additional or alternative tasks. The tasks shown in FIG. 11C need not be performed in the illustrated order, and process 1170 may be incorporated into a more comprehensive procedure or process having additional functionality not described in detail herein. For illustrative purposes, the following description of process 1100B may refer to elements mentioned above in connection with FIGS. 1-7A. In various embodiments, portions of process 1170 may be performed by different elements of systems 100-700, e.g., core system 102, the customer application interface 110, the distributed storage delivery nodes 112, etc.

Upon receiving a download request (task 1172) for a file, a download server 706 (FIG. 7) at a designated storage node may determine which of a plurality of storage servers within the node 112 is least busy (task 1174). Least busy may be measured by, for example, the lowest number of current accesses or accesses within a predetermined period of time. The server with the lowest number of accesses may then be used to serve the download request (task 1178). In one embodiment, immediately upon receiving the transfer request, the identified server's CAC is incremented by one (task 1176) to indicate it is currently handling an additional access request. After the server completes serving the request, its CAC is decremented by one. Each time the CAC is incremented or decremented the node stores a last update date (LUD) time stamp for that LFID's CAC to determine when the CAC was last changed and, hence, the number of access requests within a predetermined period of time. In this manner, the storage node performs "intra-node load balancing" among the plurality of storage servers within the storage node 700 by directing a request to a "least busy" storage server in the storage node 700. In other words, the number of simultaneous requests handled by a node is evenly distributed amongst a plurality of storage servers within the node such that no one server works harder on average than another server. It is appreciated, that this type of intra-node load balancing reduces service latencies and optimizes node performance and server longevity.

Next, the node determines whether it is "near enough" or "local" to the end user's device by comparing a geocode value associated with the user's IP address to its own geocode or, alternatively, by simply determining whether the user IP address is listed on its "serve list," as described above (inquiry task 1182). If the first storage node is determined to be "near enough" ("Yes" branch of inquiry task 1182), then the first storage node compares the number of requests it is handling to a predetermined threshold (inquiry task 1184). If the number of requests exceeds the threshold ("No" branch of inquiry task 1184), then the first storage node is determined to be too busy and the file is copied to a second storage node (task 1186). In one embodiment, the node notifies the core 102 that it is too busy, as described above, and the core thereafter instructs a second node to copy the file from the original node. Alternatively, in another embodiment, the original node can automatically identify a new node that is near enough the user and instruct the new node to copy the requested file. It is appreciated, however, that this latter embodiment requires more information and logic to be stored at the node. Subsequent requests for the file can then be directed to the second storage node to offset some of the load of the first storage node. Thus, storage nodes within the network can perform inter-node load balancing as well. If the number of requests does not exceed the threshold ("Yes" branch of inquiry task 1178), then the first storage node continues to process further file requests for that file.

Referring back to inquiry task 1182, if the storage node determines that it is not a proper node to serve the requester ("No" branch of inquiry task 1182), then the storage node notifies the core system 102. The core system 102 then determines the nearest storage node that contains the requested file based on the IP address of the end user (task 1188). A distance between the end user and the node containing the file is compared with a predetermined threshold in decision task 1190. If the threshold is not exceeded ("Yes" branch of decision task 1190), then the node identified in task 1188 process the request and process 1170 ends. Alternatively, the original node processes the current request but all subsequent requests for the same file by the same user or user similarly located as that user are processed by the new node. If the threshold is exceeded ("No" branch of decision task 1190), then the core system 102 directs the original storage node to send the file to the nearest storage node identified in task 1188 for storage (task 1192). The new nearest storage node containing the file may then process the file and notify the LFS 107 of the file's existence at the node.

Figure 12:
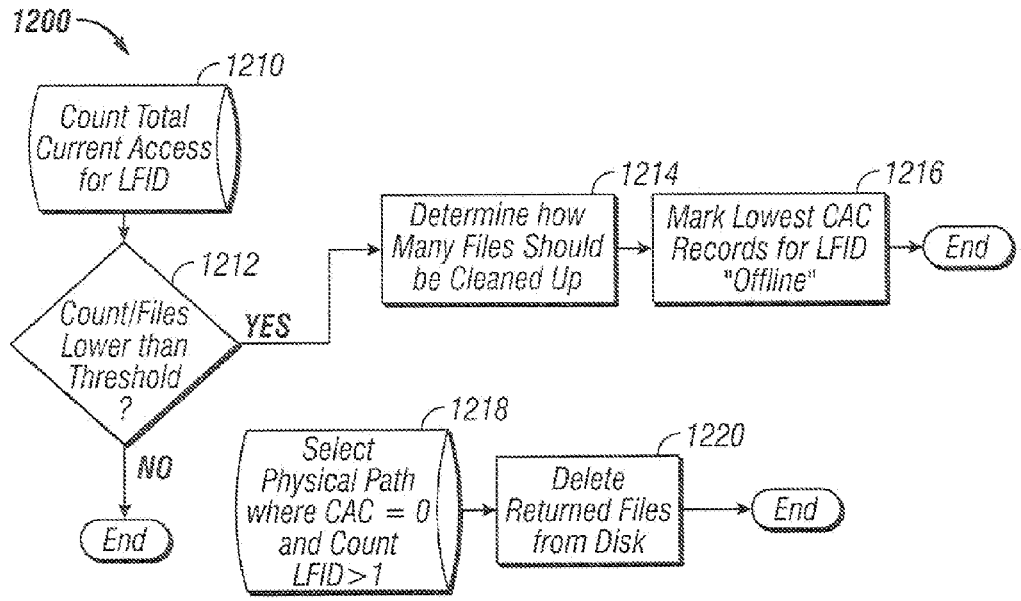
FIG. 12 illustrates a flowchart of an exemplary cleanup process in accordance with one embodiment of the invention.

When a file is stored at two or more storage servers within a node, it may be desirable to delete the file at one or more of the storage servers for de-duplication purposes. In one embodiment, a cleanup program determines if it is no longer necessary to store one or more redundant files within a node based on a current access count (CAC) associated with the LFID for the file. FIG. 12 is a flow chart of an exemplary cleanup process 1200 associated intra-node load balancing, in accordance with one embodiment of the present invention. The various tasks performed in connection with process 1200 may be implemented by software, hardware, firmware, a computer-readable medium storing computer executable instructions for performing the process method, or any combination thereof. It should be appreciated that process 1200 may include any number of additional or alternative tasks. The tasks shown in FIG. 12 need not be performed in the illustrated order, and these processes may be incorporated into a more comprehensive procedure or process having additional functionality not described in detail herein. For illustrative purposes, the following description of process 1200 may refer to elements mentioned above in connection with FIGS. 1-9. In various embodiments, portions of process 1200 may be performed by different elements of systems 100-700, e.g., core system 102, the customer application interface 110, the distributed storage delivery nodes 112, etc.

Process 1200 may begin by counting a total current access count (CAC) for an LFID associated with a file (task 1210). In this context, "current access count" refers to a number of times a logical file is currently being accessed. If the total current access count of the LFID divided by the number of physical files currently associated with the LFID is not lower than a predetermined threshold ("No" branch of inquiry task 1212), then process 1200 ends and no files are deleted If the total current access count of the LFID divided by the number of physical files currently associated with the LFID is lower than the threshold ("Yes" branch of inquiry task 1212), process 1200 determines how many files should be cleaned up by subtracting the rounded-down quotient of the threshold divided by the CAC from the current physical file count (task 1214). For example, if the total CAC is equal to 10, and the threshold is equal to 12, and the number of physical files associated with the LFID is equal 2, then the number of files to be deleted is equal to 2-(rounded down quotient of 12/10) =1. Thus, in this example, the number of redundant files to be deleted is equal to 1. Next, the corresponding number of physical files, which have the lowest CAC associated with them, are marked offline so no new connections are made to those files and existing connections are closed after the current transfers are completed (task 1216). A separate process determines which files are marked offline and are no longer being accessed (i.e., CAC is equal to zero) (task 1218) and deletes those files from the disk (task 1220).

In a further embodiment the minimum number of physical files may be set to a number greater than one. In this scenario, the formula for task 1214 may be modified to ensure that a specific number of physical files are always maintained for each logical file. As would be understood by one of ordinary skill in the art, any threshold value may be selected based on the operating and/or performance capabilities of the storage servers within the node, to control the loads on each server. In this manner, the number of redundant copies of a file stored in a node is continuously and automatically adjusted based at least in part on the number of access requests for that file and the operating/performance capabilities of the servers within the node.

Although the internet media file system is described in the context of storing, accessing and manipulating files via the internet, it is understood that the invention is applicable within any type of communications network (e.g., LAN, WAN, etc.). However, for illustrative purposes, the data file system and method of the present invention is described as an internet media file system (IMFS). The IMFS 108 can have a variety of functions and uses. Some exemplary uses are discussed below.

As an example, although the IMFS 108 has been described above in connection with SDN storage nodes 112, it is understood that the IMFS 108 may be used with various types of physical storage devices having a variety of storage network configurations. Thus, the IMFS 108 need not be used exclusively with distributed storage delivery nodes 112, but can be used with other types of memory devices as well.

The IMFS 108 is a file system that can enable users to store, retrieve, and manipulate files from a remote location using a rich set of Web Service API's. File system operations require a caller (i.e., a requester such one of the end users 114) to be authenticated. For example, calls into IMFS 108 may require a session token which can be obtained by a logical call. In general, paths can be specified as either absolute or relative to an account's root folder.

The following are some exemplary Web Service interfaces for IMFS.

A CopyFiles function or function is used to copy a file from one location to another. The CopyFiles function can be used to copy one or more files to a given folder.

A CopyFolders function is used to copy a folder from one location to another. The CopyFolders function can be used to copy one or more folders.

A CreateFolders function is used to create a new folder at the specified location.

A DeleteFiles function is used to remove one or more files.

A DeleteFolders function is used to remove one or more folders.

A ListFolder function is used to page the content of a given folder.

A MoveFiles function is used to move a file from one location to another. The MoveFiles function can be used to move one or more files to a given folder.

A MoveFolders function is used to move a folder from one location to another. The MoveFolders function can be used to move one or more folders.

A RenameFile function is used to rename a file from one name to another.

A RenameFolder function is used to rename a folder from one name to another.

In one embodiment, the IMFS 108 can correlate the physical files with their corresponding customers. Thus, the IMFS 108 can keep track of what content is stored in the distributed storage delivery nodes 112, where it is stored in the distributed storage delivery nodes 112, and who has access to the content. The IMFS 108 may map the customer to a IMFS Web Services in order to keep track of a customer's file and provide access for the customer and/or customer's clients.

Figure 13:
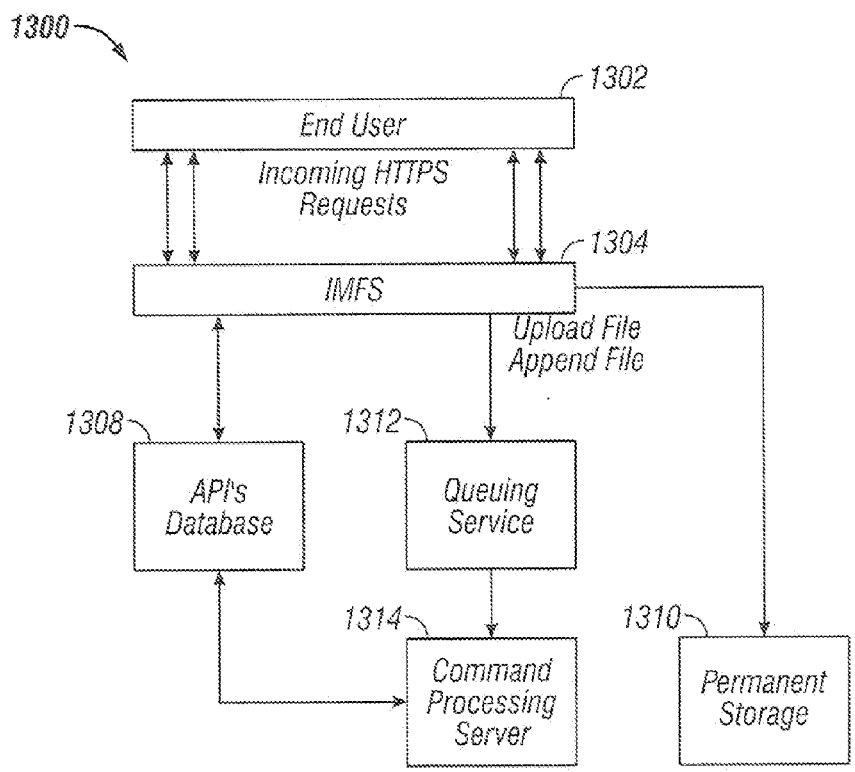
FIG. 13 illustrates a flowchart of an exemplary process of storing files using an internet media file system (IMFS) in accordance with one embodiment of the invention.

FIG. 13 illustrates an exemplary IMFS data flow 1300 in accordance with one embodiment of the invention.

As shown in FIG. 13 an end user 1302 can make a request to the IMFS Web Services 1304 to access the IMFS. IMFS Web Services 1304 may provide a set of API's that can allow an end user 1302 to upload files to their IMFS and for manipulating the metadata An exemplary method of providing the API's is using the SOAP protocol, however an HTTP upload interface will also be provided. The metadata types may include, without limitation, image files, width, height, video file, duration, bit rate, frame rate, audio files, title, artist, album, genre, track, and the like. The IMFS can have many function to manipulate metadata, including, without limitation:

A DeleteAllMetadata function for removing all metadata from a file.

A DeleteMetadata function for removing specified metadata from a file.

A GetMetadata function for retrieving all metadata from a file.

A SetMetadata function for setting specified metadata for a file.

A DeleteAllTags function for removing all tags from a file.

A DeleteTags function for removing specified tags from a file.

A GetTags function for retrieving all tags from a file.

A SetTags function for setting specified tags for a file.

IMFS Web Services 1304 may include interfaces to the IMFS to allow end users 1302 to, for example, upload, append, copy, delete, move, and rename files and folders. In one embodiment, the IMFS Web Services 1301 may implement the industry standard REST and SOAP protocols for implementing the APIs to the functions. The interfaces to the IMFS may include, without limitation, A CopyFiles function used to copy a file from one location to another. The CopyFiles function can be used to copy one or more files to a given folder.

A CopyFolders function used to copy a folder from one location to another. The CopyFolders function can be used to copy one or more folders.

A CreateFolders function used to create a new folder at the specified location.

A DeleteFiles function used to remove one or more files.

A DeleteFolders function used to remove one or more folders.

A ListFolder function used to page the content of a given folder.

A MoveFiles function used to move a file from one location to another. The MoveFiles function can be used to move one or more files to a given folder.

A MoveFolders function used to move a folder from one location to another. The MoveFolders function can be used to move one or more folders.

A RenameFile function used to rename a file from one name to another.

A RenameFolder function used to rename a folder from one name to another.

Furthermore, end users 1302 can retrieve a listing of their files and also associate user defined tags and metadata.

With further reference to FIG. 13, the IMFS Web Services 1304 may communicate with an API database 1308 to obtain the IMFS Web Services API's. After a device used by the end user 1302 receives an IMFS Web Services API, the device may use the API to access files through the command processing servers 214 (FIG. 2). Unless the end user 1302 is requesting to append or upload a file, the IMFS Web Services 1304 returns the IMFS Web Services API to the end user 1302 as a response to the request.

If the end user 1302 requests to upload or append a file with, for example an "Upload File" command, then the IMFS Web Services 1304 writes portions (e.g., bytes) of the user's file to permanent storage 1310. The IMFS Web Services 1304 may then submit the "Upload File" command to the message queuing service 1312 (as explained in more detail below), and return a response to the end user 1302 with the status of the command.

The "Upload File" command may be used to upload a file in its entirety. If the path does not exist it can be created. The maximum file size for uploading a file using this command may be, for example, about 2 GB. If the file is larger than about 2 GB, then the append file method may be used. For example, if the filename is "Vacations/2007/Hawaii/beachDay1.jpg", then when the file is done uploading, the file would be added to the file system as Vacations/2007/Hawaii/beachDay1.jpg". The IMFS Web Services 1304 may create the folders that do not exist in this scenario using standard operating system file operations. The "Append File" command can be used to add data to the uploaded file in parts.

When an end user 1302 uploads a file using the API's append file method and upload file method, then there may be other actions that occur within the IMFS Web Services 1304. For example, as soon as the last portion (i.e., last byte) of the file has been written to the permanent storage 1310, the IMFS Web Services 1304 may interact with the database 1308 and update the end user's file system. At that point, the end user 1302 may complete access to their file. The end user 1302 can download, copy, move, delete, rename, and set tag and metadata information for the file. The command processing service 1314 may process this file, and extract industry standard metadata from image, video, audio files, and the like.

In one embodiment, the command processing service 1314 can be a Windows Service operable to be a scalable and extensible solution for executing system wide tasks for the IMFS Web Services 1304. In alternative embodiments, the command processing service 1314 can be implemented as an operating system daemon operable to be a scalable and extensible solution for executing system wide tasks for the IMFS Web Services 1304. The service 1314 can function as a generic framework for computations that can be completed asynchronously.

In one embodiment, a web-based tool may allow the IMFS to get a real-time snapshot of all activity occurring on a given server running the command processing service 1314. This can be very beneficial for troubleshooting purposes, and to have an overall view of the number of files that are being uploaded over time.

One of the purposes of the command processing service 1314 is, for example, to calculate the MD5 hash for the purpose of physical file de-duplication as explained above. It can also be responsible for extracting metadata from image, video, and audio files in order to provide the end user 1302 with more information about their files. Examples of this type of metadata are image width and height, video frame rate, the artist and album for an audio file, and the like.

The command processing service 1314 may function to run regularly scheduled maintenance jobs for customers (end users) who have unreported usage, clean up aborted upload files, and provide system resource information such as available storage to the IMFS database 1308.

The command processing service 1314 may run on one or more servers located throughout various nodes. As processing requirements grow, processing servers can easily be added to assist in balancing the system 100 load. All processing servers running the command processing service 1314 may be independent from any other processing server (i.e., one processing server may have has no idea that any other processing server exists). Load balancing amongst storage node servers or between storage nodes may be automatic, as explained above.

The command processing service 1314 may wait for a command, and then execute it. When it is not executing a command, it may be idle. The mechanism by which the command processing service 1314 receives these commands is a queuing service such as queuing service 1312. In one embodiment, the queuing service 1312 may comprise an MSMQ service. The queuing service 1312 may be configured in a clustered set of nodes in the node with complete failover capability. Therefore, if one of the queuing service cluster nodes happened to fail, it would automatically fail-over to another storage delivery node without any data loss. The queuing service 1312 service may also be configured to have data recovery if for some reason the queuing service 1312 service needs to be stopped and/or restarted. All data currently stored in the queue is automatically serialized to disk.

As mentioned above, a command may be sent to the queuing service 1312 from the IMFS Web Services 1306 when the end user 1302 uploads a file, as will be explained below. Once a command arrives at the queuing service 1312, it can automatically be retrieved from one command processing service 1314 that is available to receive that command for processing. In one embodiment, commands are asynchronously "pulled" from a command processing service 1314 not "pushed" to a command processing service 1314. Once a command is retrieved, it can automatically be removed from the queuing service 1312. Commands sent to the queuing service 1312 may have a priority associated with them. In other words, a command may be submitted to the queuing service 1312 and be moved 'to the head of line' so that it is received ahead of other commands already in the queuing service 1312. The command processing service 1314 may be operable to take full advantage of this feature.

Each command processing service 1314 can, for example, be initialized with about 10 processing threads on a given server. Therefore, each processing server can process about 10 commands simultaneously and each command is executed totally asynchronous from any other command. The number of processing threads is configurable. Once a processing thread has completed executing the command, it waits to receive another command from the queuing service 1312. The threads are either executing a command or waiting to receive another command until the service is terminated.

Under optimal conditions, commands submitted to queuing service 1312 are taken off the queue to be processed immediately. However, under heavy load conditions, the processing servers may not be able to process all commands as fast as they are being submitted. As a result, commands may have to wait in the queue longer than desired before getting processed. In this case, additional processing servers can be added to further distribute the system load and reduce processing delays.

Standard commands may asynchronously be sent to the queuing service 1312 and be asynchronously executed by a command processing service 1314. The standard commands may include, without limitation: a "BaseCommand", a "Scheduler" command, a "Media" command, a "File Ingestion" command, a "Multi Node File Copy" command, a "Partial File Update" command, an "Add Physical File" command, a "Get Upload Location" command, and the like.

A "Get Upload Location" command can be used to determine which distributed storage delivery nodes 112 a file may be uploaded to. The "Get Upload Location" may return an IP address for the distributed storage delivery nodes 112 (FIG. 1) and an upload token.

It may be possible that a command submitted to processing service 1314 fails to execute. One scenario would be network congestion. If a command fails, the command processing service 1314 may resubmit this command to the queuing service 1312, but into a special separate queue designed for holding failed commands. Failed commands may not in any way affect a user's ability to download or manipulate the files. It may mean that a file may not have an MD5 hash and its embedded metadata, if applicable, associated with it. Failed commands can be re-processed at an information technologist's discretion once the system/network problem has been resolved.

Figure 14:
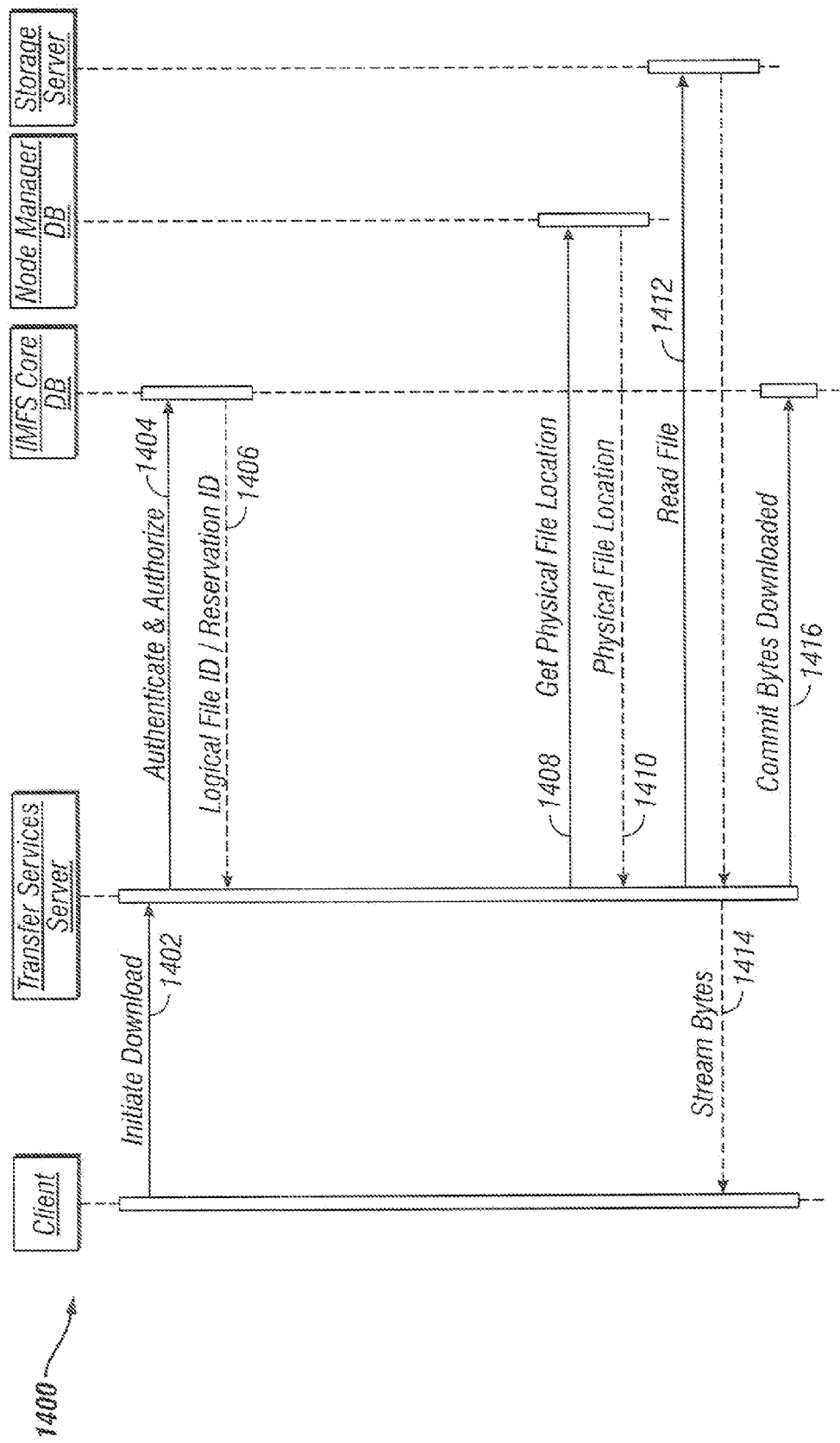
FIG. 14 illustrates an exemplary download sequence that may be implemented using an IMFS core database in accordance with one embodiment of the invention.

FIG. 14 illustrates an exemplary download sequence 1400 that may be implemented using IMFS core database in accordance with one embodiment. At step 1402, the client initiates download request to the download node to which it was redirected by the core 102 (FIG. 1). Next, at step 1404, a transfer services server 707 (FIG. 7) asks the IMFS core database to authenticate the user and authorize the download given a session token, the file path, and the number of bytes being requested. If the request meets all restrictions placed on this account such as file size limit or bandwidth limit, a reservation will be made against the account for the number of download bytes requested. The database then returns the LFID associated with the user's virtual file path and a reservation ID for the download at step 1406. Next, the transfer services server asks the local node manager database for the physical location of the file given the logical file ID at step 1408 and the physical location is provided in step 1410.

The transfer services server reads the file content from the physical location at step 1412 and the transfer services server streams the content to the client at step 1414. After the transfer services server completed serving the client's request, it commits the actual bytes transferred for the reservation ID to the IMFS database at step 1416.

FIG. 15 illustrates an exemplary relocated file download sequence 1500 that may be implemented using IMFS core database in accordance with one embodiment. At step 1502, a client sends a download request to a first download node. A transfer services server receives this request and then asks the IMFS Core DB to authenticate the user and authorize the download given a session token, the file path, and the number of bytes being requested at step 1504. The DB responds with an error indicating that the requested file is no longer available at the first node and what the current optimum download node is at step 1506. The transfer services server at the first download node then redirects the client to a new, second download node at step 1508, using the original requested URL with the node address replaced. At a next step 1510, the client initiates the same request to a transfer services server within the second node. The remaining sequence of process 1500 can be similar to steps 1404 through 1416 of FIG. 14.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

In this document, the term "module" as used herein, refers to software, firmware, hardware, and any combination of these elements for performing the associated functions described herein. Additionally, for purpose of discussion, the various modules are described as discrete modules; however, as would be apparent to one of ordinary skill in the art, two or more modules may be combined to form a single module that performs the associated functions according embodiments of the invention.

In this document, the terms "computer program product", "computer-readable medium", and the like, may be used generally to refer to media such as, memory storage devices, or storage unit. These, and other forms of computer-readable media, may be involved in storing one or more instructions for use by processor to cause the processor to perform specified operations. Such instructions, generally referred to as "computer program code" (which may be grouped in the form of computer programs or other groupings), which when executed, enable the computing system.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to", or other like phrases in some instances shall not be read to mean that the narrower case is intended or required in instances where such broadening phrases may be absent.

What is claimed is:

1. A method for balancing loads among a plurality of data storage devices, comprising:
   receiving a request from a user device to download a data file;
   identifying a first set of storage devices containing the requested data file, wherein the first set comprises first and second storage devices each storing a copy of the requested data file;
   determining whether one or more redundant copies of the requested file from the first set of storage devices should be deleted based at least in part on a number of current access requests for the file, wherein determining whether one or more redundant copies of the requested file should be deleted comprises:
   determining whether a quotient, provided by a total number of current access requests for the file divided by a total number of copies of the files stored in the first set, is lower than a predetermined threshold, wherein if the quotient is lower than the predetermined threshold, the one or more redundant copies are designated to be deleted.

2. The method of claim 1 further comprising determining how many redundant copies to delete based on the formula: N=CFC−(T/CAC), where N is the number of redundant copies to delete, CFC is the total number of copies of the requested file stored in the first set, T is a predetermined threshold selected based on a desired average load upon the first set of storage devices, and CAC is the total number of current access requests for the data file.

3. The method of claim 2 further comprising:
   designating the N redundant files to be deleted as "offline" so they cannot be accessed; and
   deleting the N redundant files as a backend process which is transparent to end users who access files from the first set of storage devices.

4. The method of claim 2 wherein the N redundant copies designated for deletion comprise the N most recently stored copies of the data file.

5. A system for balancing loads among a plurality of storage servers within a storage node, comprising:
   a node manager server for receiving a request from a user device to download a data file;
   a plurality of storage servers contained within a first storage node for storing one or more copies of the data file;
   a transfer server coupled to the plurality of storage servers for downloading the data file requested by users;
   wherein the node manager server comprises:
      a first module for receiving the request from the user device to download the data file;
      a second module for identifying a first set of storage servers among the plurality of storage servers in the node containing the requested data file, wherein the first set comprises first and second storage servers each storing a copy of the requested data file;
   a third module for determining whether one or more redundant copies of the requested file from the first set of storage servers should be deleted based at least in part on a number of current access requests for the file, wherein fifth module comprises:
   a fourth module for determining whether a quotient, provided by a total number of current access requests for the file divided by a total number of copies of the files stored in the first set, is lower than a predetermined threshold, wherein if the quotient is lower than the predetermined threshold, the one or more redundant copies are designated to be deleted.

6. The system of claim 5 further comprising a fifth module for determining how many redundant copies to delete based on the formula: N=CFC−(T/CAC), where N is the number of redundant copies to delete, CFC is the total number of copies of the requested file stored in the set, T is a predetermined threshold selected based on a desired average load upon the set of storage devices, and CAC is the total number of current access requests for the data file.

7. The system of claim 6 further comprising:
   a sixth module for designating the N redundant files to be deleted as "offline" so they cannot be accessed; and
   a seventh module for deleting the N redundant files as a backend process which is transparent to the user.

8. The system of claim 6 wherein the N redundant copies designated for deletion comprise the N most recently stored copies of the data file.

9. A non-transitory computer readable medium storing computer executable instructions that when executed perform a process for balancing loads among a plurality of storage servers within a storage node, the instructions comprising:
   a first code module for receiving a request from a user device to download a data file;
   a second code module for identifying a first set of storage servers among a plurality of storage servers in a first node containing the requested data file, wherein the first set comprises first and second storage servers each storing a copy of the requested data file;

a third code module for determining whether one or more redundant copies of the requested file from the first set of storage servers should be deleted based at least in part on a number of current access requests for the file, wherein fifth code module comprises:

a fourth code module for determining whether a quotient, provided by a total number of current access requests for the file divided by a total number of copies of the files stored in the first set, is lower than a predetermined threshold, wherein if the quotient is lower than the predetermined threshold, the one or more redundant copies are designated to be deleted.

10. The non-transitory computer readable medium of claim 9 further comprising a fifth code module for determining how many redundant copies to delete based on the formula: $N=CFC-(T/CAC)$, where N is the number of redundant copies to delete, CFC is the total number of copies of the requested file stored in the first set, T is a predetermined threshold selected based on a desired average load upon the set of storage devices, and CAC is the total number of current access requests for the data file.

11. The non-transitory computer readable medium of claim 10 further comprising:
a sixth code module for designating the N redundant files to be deleted as "offline" so they cannot be accessed; and
a seventh code module for deleting the N redundant files as a backend process which is transparent to the user.

12. The non-transitory computer readable medium of claim 10 wherein the N redundant copies designated for deletion comprise the N most recently stored copies of the data file.

* * * * *